US012611319B2

(12) United States Patent
Kartholl et al.

(10) Patent No.: US 12,611,319 B2
(45) Date of Patent: Apr. 28, 2026

(54) INSERTER FOR GLENOSPHERE

(71) Applicant: HOWMEDICA OSTEONICS CORP., Mahwah, NJ (US)

(72) Inventors: Matthew Victor Kartholl, Fort Wayne, IN (US); Charles L. Penninger, Warsaw, IN (US); Ryan D. Koepke, Fort Wayne, IN (US); Austin Wyatt Mutchler, Warsaw, IN (US)

(73) Assignee: HOWMEDICA OSTEONICS CORP., Mahwah, NJ (US)

( * ) Notice: Subject to any disclaimer, the term of this patent is extended or adjusted under 35 U.S.C. 154(b) by 682 days.

(21) Appl. No.: 17/906,371

(22) PCT Filed: Apr. 19, 2021

(86) PCT No.: PCT/US2021/027891
§ 371 (c)(1),
(2) Date: Sep. 15, 2022

(87) PCT Pub. No.: WO2021/216405
PCT Pub. Date: Oct. 28, 2021

(65) Prior Publication Data
US 2023/0172730 A1 Jun. 8, 2023

Related U.S. Application Data

(60) Provisional application No. 63/012,434, filed on Apr. 20, 2020.

(51) Int. Cl.
*A61F 2/46* (2006.01)
*A61F 2/30* (2006.01)
*A61F 2/40* (2006.01)
(52) U.S. Cl.
CPC ........ *A61F 2/4637* (2013.01); *A61F 2/30749* (2013.01); *A61F 2/4081* (2013.01);
(Continued)

(58) Field of Classification Search
CPC .................................................. A61F 2/4609
See application file for complete search history.

(56) References Cited

U.S. PATENT DOCUMENTS 2,370,336 A * 2/1945 Wallace ................ B25B 31/005
269/48.3
2,669,896 A * 2/1954 Clough ................. B25B 23/105
81/453

(Continued)

FOREIGN PATENT DOCUMENTS

AU 2003270164 A1 4/2004
CN 105411661 A 3/2016

(Continued)

OTHER PUBLICATIONS

Partial Supplemental European Search Report issued in connection with European Patent Application No. 21791786.3, Feb. 16, 2024, 14 pages.

(Continued)

*Primary Examiner* — David W Bates
(74) *Attorney, Agent, or Firm* — DUANE MORRIS LLP

(57) ABSTRACT

A glenosphere handling tool, which can be an impactor, is provided that includes an elongate body and a retention portion. The retention portion is disposed at a distal end of the elongate body. The retention portion includes a plurality of wall segments of the elongate body separated from each other by one or more slots. The slot(s) extends proximally from the distal end of the elongate body. The retention portion also includes an enlarged periphery at the distal end of the elongate body. The enlarged periphery comprising a proximally facing edge configured to engage an inner wall surface of a glenosphere. The retention portion is configured such that when the retention portion is in a free state the proximally facing edge faces and may contact a surface of a glenosphere to retain the glenosphere. The retention por- (Continued)

tion is configured to be deflected at the distal end of the elongate body such that the enlarged periphery has a reduced profile for separating the handling tool from a glenosphere.

37 Claims, 22 Drawing Sheets

(52) U.S. Cl.
CPC ................ *A61F 2002/4085* (2013.01); *A61F 2002/4681* (2013.01)

(56) References Cited

U.S. PATENT DOCUMENTS

| | | | | |
|---|---|---|---|---|
| 5,059,196 | A * | 10/1991 | Coates | A61F 2/461 |
| | | | | 269/48.3 |
| 5,116,339 | A * | 5/1992 | Glock | A61F 2/4609 |
| | | | | 606/81 |
| 5,158,331 | A * | 10/1992 | Wesselski | F16B 2/185 |
| | | | | 294/94 |
| 5,169,399 | A * | 12/1992 | Ryland | A61F 2/4609 |
| | | | | 606/91 |
| 5,171,243 | A * | 12/1992 | Kashuba | A61F 2/34 |
| | | | | 606/86 R |
| 5,171,313 | A * | 12/1992 | Salyer | A61B 17/1666 |
| | | | | 606/86 R |
| 5,486,181 | A * | 1/1996 | Cohen | A61F 2/34 |
| | | | | 606/100 |
| 5,540,697 | A * | 7/1996 | Rehmann | A61F 2/4609 |
| | | | | 606/100 |
| 5,683,399 | A * | 11/1997 | Jones | A61F 2/4609 |
| | | | | 606/91 |
| 5,782,830 | A * | 7/1998 | Farris | A61F 2/30767 |
| | | | | 606/99 |
| 6,102,953 | A | 8/2000 | Huebner | |
| 6,168,627 | B1 | 1/2001 | Huebner | |
| 6,205,884 | B1 | 3/2001 | Foley et al. | |
| 6,626,913 | B1 * | 9/2003 | McKinnon | A61F 2/367 |
| | | | | 606/86 R |
| 7,004,946 | B2 * | 2/2006 | Parker | A61F 2/4609 |
| | | | | 606/99 |
| 7,235,082 | B2 * | 6/2007 | Bartish | A61F 2/4611 |
| | | | | 606/99 |
| 7,341,593 | B2 | 3/2008 | Auxepaules et al. | |
| 7,621,921 | B2 * | 11/2009 | Parker | A61F 2/34 |
| | | | | 606/91 |
| 8,157,808 | B2 | 4/2012 | Keller | |
| 8,277,457 | B1 * | 10/2012 | Burgi | A61F 2/4609 |
| | | | | 606/81 |
| 8,303,601 | B2 * | 11/2012 | Bandeira | A61B 17/025 |
| | | | | 606/90 |
| 8,556,900 | B2 | 10/2013 | Yoko et al. | |
| 8,585,709 | B2 * | 11/2013 | Burgi | A61F 2/4609 |
| | | | | 606/91 |
| 8,657,824 | B2 | 2/2014 | Sharp et al. | |
| 8,657,833 | B2 | 2/2014 | Burgi et al. | |
| 8,961,528 | B2 * | 2/2015 | Burgi | A61F 2/4609 |
| | | | | 606/91 |
| 9,186,484 | B2 * | 11/2015 | Defossez | A61B 17/8872 |
| 9,283,075 | B2 | 3/2016 | Wiley et al. | |
| 9,398,929 | B2 | 7/2016 | Young et al. | |
| 9,439,780 | B2 * | 9/2016 | Witt | A61F 2/4609 |
| 9,456,828 | B2 | 10/2016 | Kerboul et al. | |
| 9,554,810 | B2 * | 1/2017 | Tsukayama | G05G 1/04 |
| 9,782,154 | B2 | 10/2017 | Slade et al. | |
| 10,245,161 | B2 | 4/2019 | Bonin et al. | |
| 10,398,569 | B2 | 9/2019 | Jaumard | |
| 10,492,927 | B2 | 12/2019 | Chenaux | |
| 12,414,811 | B2 * | 9/2025 | Childs | A61B 17/320016 |
| 12,478,412 | B2 * | 11/2025 | Cromer | A61B 17/7086 |
| 2006/0074418 | A1 * | 4/2006 | Jackson | A61B 17/7086 |
| | | | | 606/264 |
| 2006/0129238 | A1 * | 6/2006 | Paltzer | A61F 2/447 |
| | | | | 606/90 |
| 2007/0093897 | A1 * | 4/2007 | Gerbec | A61F 2/4611 |
| | | | | 600/431 |
| 2007/0173945 | A1 | 7/2007 | Wiley et al. | |
| 2008/0021481 | A1 * | 1/2008 | Burgi | A61F 2/4609 |
| | | | | 606/99 |
| 2008/0255568 | A1 | 10/2008 | Tornier et al. | |
| 2008/0262503 | A1 * | 10/2008 | Muller | A61F 2/4612 |
| | | | | 606/99 |
| 2009/0112219 | A1 * | 4/2009 | Daniels | A61F 2/4607 |
| | | | | 606/99 |
| 2009/0177240 | A1 | 7/2009 | Perez | |
| 2010/0191246 | A1 * | 7/2010 | Howald | A61F 2/34 |
| | | | | 623/22.21 |
| 2011/0046625 | A1 | 2/2011 | Boileau et al. | |
| 2012/0316569 | A1 | 12/2012 | Fenton et al. | |
| 2013/0226186 | A1 * | 8/2013 | Burgi | A61F 2/4609 |
| | | | | 606/91 |
| 2013/0261751 | A1 | 10/2013 | Lappin | |
| 2013/0289738 | A1 | 10/2013 | Humphrey | |
| 2013/0304228 | A1 | 11/2013 | Phipps | |
| 2014/0081283 | A1 * | 3/2014 | Liang | A61F 2/4609 |
| | | | | 606/99 |
| 2014/0180430 | A1 * | 6/2014 | Gillman | A61B 17/1746 |
| | | | | 606/100 |
| 2014/0188232 | A1 | 7/2014 | Metcalfe et al. | |
| 2014/0207123 | A1 * | 7/2014 | Mueller | A61F 2/4607 |
| | | | | 606/1 |
| 2015/0094728 | A1 | 4/2015 | Rhoades et al. | |
| 2015/0105783 | A1 * | 4/2015 | Clarke | A61F 2/4609 |
| | | | | 606/91 |
| 2016/0228262 | A1 * | 8/2016 | Bailey | A61F 2/34 |
| 2016/0310176 | A1 | 10/2016 | Van Dyke et al. | |
| 2017/0128097 | A1 | 5/2017 | Grutta et al. | |
| 2017/0340449 | A1 | 11/2017 | Deransart et al. | |
| 2018/0028202 | A1 | 2/2018 | Nelson et al. | |
| 2018/0353248 | A1 | 12/2018 | Bowling et al. | |
| 2019/0021879 | A1 | 1/2019 | Sweitzer | |
| 2019/0216615 | A1 | 7/2019 | Paterson et al. | |
| 2019/0269423 | A1 | 9/2019 | Termanini | |
| 2020/0253648 | A1 | 8/2020 | Langdale et al. | |
| 2020/0315808 | A1 | 10/2020 | Goldberg et al. | |

FOREIGN PATENT DOCUMENTS

| | | | | | |
|---|---|---|---|---|---|
| CN | 209808650 | | 12/2019 | | |
| EP | 1549258 | B1 | 4/2011 | | |
| GB | 2299758 | A | 10/1996 | | |
| HU | 192924 | B * | 8/1987 | ........... A61F 2/4609 |
| JP | 2009523578 | A | 6/2009 | | |
| WO | 2004024029 | A2 | 3/2004 | | |
| WO | 2004069107 | A1 | 8/2004 | | |
| WO | 2007124607 | A1 | 11/2007 | | |
| WO | 2008116203 | A2 | 9/2008 | | |
| WO | 2012096965 | A1 | 7/2012 | | |
| WO | 2016094739 | | 6/2016 | | |
| WO | 2018109379 | | 6/2018 | | |
| WO | 2019169357 | | 9/2019 | | |

OTHER PUBLICATIONS

Extended European Search Report issued in connection with European Patent Application No. 21791786.3, May 7, 2024, 12 pages.
Extended European Search Report issued in connection with European Patent Application No. 22772355.8, Dec. 9, 2024, 7 pages.
International Preliminary Report on Patentability issued in connection with International Patent Application No. PCT/US2022/070304, Sep. 28, 2023, 11 pages.
International Search Report and Written Opinion issued in connection with International Patent Application No. PCT/US2021/027891, Oct. 20, 2021, 18 pages.
First Examination Report issued in connection with Australian Patent Application No. 202159279, Nov. 3, 2023, 11 pages.

(56)            References Cited

OTHER PUBLICATIONS

First Office Action issued in connection with Japanese Patent
Application No. 2023-557181, Jul. 30, 2024, 6 pages.

\* cited by examiner

108

116

D

INSERTER FOR GLENOSPHERE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 C.F.R. § 1.57.

BACKGROUND OF THE INVENTION

Field of the Invention

This application is directed to an instrument for handling, delivering and/or implanting a convex articular component (e.g., a glenosphere) during a shoulder arthroplasty procedure.

Description of the Related Art

Arthroplasty is the standard of care for the treatment of advanced shoulder joint problems, such as severe arthritis. Shoulder arthroplasty can replicate the anatomical form of a joint, with a spherical component mounted on the proximal humerus and a concave surface mounted on the glenoid region of the scapula. Certain patients benefit from a reverse shoulder reconstruction in which a spherical component is mounted to the scapula and a concave surface is positioned on the proximal humerus.

A surgical procedure to install the spherical component can involve handing the spherical component and also connecting the spherical component to a baseplate implanted on the scapula. Reducing the complexity and time involved in these surgical steps is to be desired. Surgical tools for handling, delivering and/or implanting articular components should be simple to use, allowing for heightened placement accuracy and providing improved patient outcomes.

SUMMARY OF THE INVENTION

Accordingly, there is a need for improved surgical tools for handling and implanting, e.g., impacting, glenospheres and other joint arthroplasty articular bodies.

In one embodiment, an impactor is provided for coupling a glenosphere to a baseplate disposed in or on a human scapula. The impactor has a handle assembly that has a proximal end and a distal end. The handle assembly also includes an outer elongate body, an inner elongate body and an actuator. The outer elongate body extends between the proximal end and the distal end. The inner elongate body extends between the proximal end and the distal end. The inner elongate body is slideably disposed within the outer elongate body. The inner elongate body has a lumen disposed therethrough and a deflectable tip portion disposed at a distal end thereof. The actuator is configured to slide the inner elongate body relative to the outer elongate body to extend the deflectable tip portion from a retracted position, e.g., relative to a distal end of the outer elongate body. The deflectable tip portion is configured to be un-deflected within a cavity of a glenosphere and to apply a force to the glenosphere, e.g., a radially outward and/or a proximally oriented force.

In another embodiment, a glenosphere impactor is provided that includes an outer impactor assembly, an inner impactor assembly, a lumen disposed through the inner elongate body, and an actuator. The outer impactor assembly has an outer elongate body, a handle disposed at a proximal portion of the glenosphere impactor, and an impaction tip at a distal portion of the glenosphere impactor. The inner impactor assembly has an inner elongate body and a deflectable distal portion. The inner elongate body is slideably disposed within the outer elongate body. The lumen is disposed through the inner elongate body and the deflectable distal portion disposed at a distal end thereof. The actuator is configured to slide the inner elongate body relative to the outer elongate body to extend the deflectable distal portion distally from the impaction tip. The deflectable distal portion is configured to be deflected within a cavity of a glenosphere and to apply a force to the glenosphere toward the handle of the outer impactor assembly.

In another embodiment, a glenosphere handling tool is provided that includes an elongate body and a retention portion. The elongate body has a proximal end and a distal end. The retention portion is disposed at the distal end of the elongate body. The retention portion includes a plurality of wall segments of the elongate body separated from each other by a slot. The slot extends from a proximal end of the slot to a distal end of the slot at the distal end of the elongate body. The retention portion also includes an enlarged periphery at the distal end of the elongate body. The enlarged periphery comprising a proximally facing edge configured to engage an inner wall surface of a glenosphere. The retention portion is configured such that the when the retention portion is in a free state the proximally facing edge faces and may contact a surface of a glenosphere to retain the glenosphere. The retention portion is configured to be deflected at the distal end of the elongate body such that the enlarged periphery has a reduced profile for separating the handling tool from a glenosphere.

In another embodiment, a method of handling a glenosphere is provided. A glenosphere is provided that has a convex articular surface, a concave interior space, and an opening providing access from the convex articular surface to the concave interior space. A tip of an elongate member of a handling tool is extended through the opening while a distal portion of the tip is in a lower profile configuration. The tip of the elongate member is actuated such that a proximally facing surface thereof has a profile larger than the opening. A proximally oriented force is applied to the glenosphere to hold the glenosphere against a tip of the handling tool.

In another embodiment a glenoid implant is provided that includes a baseplate and an anchor member. The anchor member can extend medially from a medial side of the baseplate. The anchor member can be configured to be embedded in a scapula medially of the glenoid surface of the scapula. The glenoid implant includes a lumen disposed through the anchor member. The lumen extends from a lateral portion to a medial portion. The lumen can extend entirely from a lateral side to a medial side. The lumen can provide access for a glenosphere inserter tool control member, such as a surgical wire. The glenosphere inserter tool control member can be advanced from a lateral side of the glenoid implant, e.g., from a lateral side of the baseplate, to a medial side of the glenoid implant, e.g., to a medial side of the anchor member. In some variations the lumen extends medially from a lateral side and may extend to a terminus forming a blind hole. The glenoid implant can have a locking screw that is pre-assembled with a glenosphere. The locking screw can have a lumen disposed therethrough, e.g., from a lateral side to a medial side. The locking screw can provide access to a lumen in the anchor member of the glenoid implant.

BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

DETAILED DESCRIPTION OF THE PREFERRED EMBODIMENT

While the present description sets forth specific details of various embodiments, it will be appreciated that the description is illustrative only and should not be construed in any way as limiting. Furthermore, various applications of such embodiments and modifications thereto, which may occur to those who are skilled in the art, are also encompassed by the general concepts described herein. Each and every feature described herein, and each and every combination of two or more of such features, is included within the scope of the present invention provided that the features included in such a combination are not mutually inconsistent.

Figure 1:
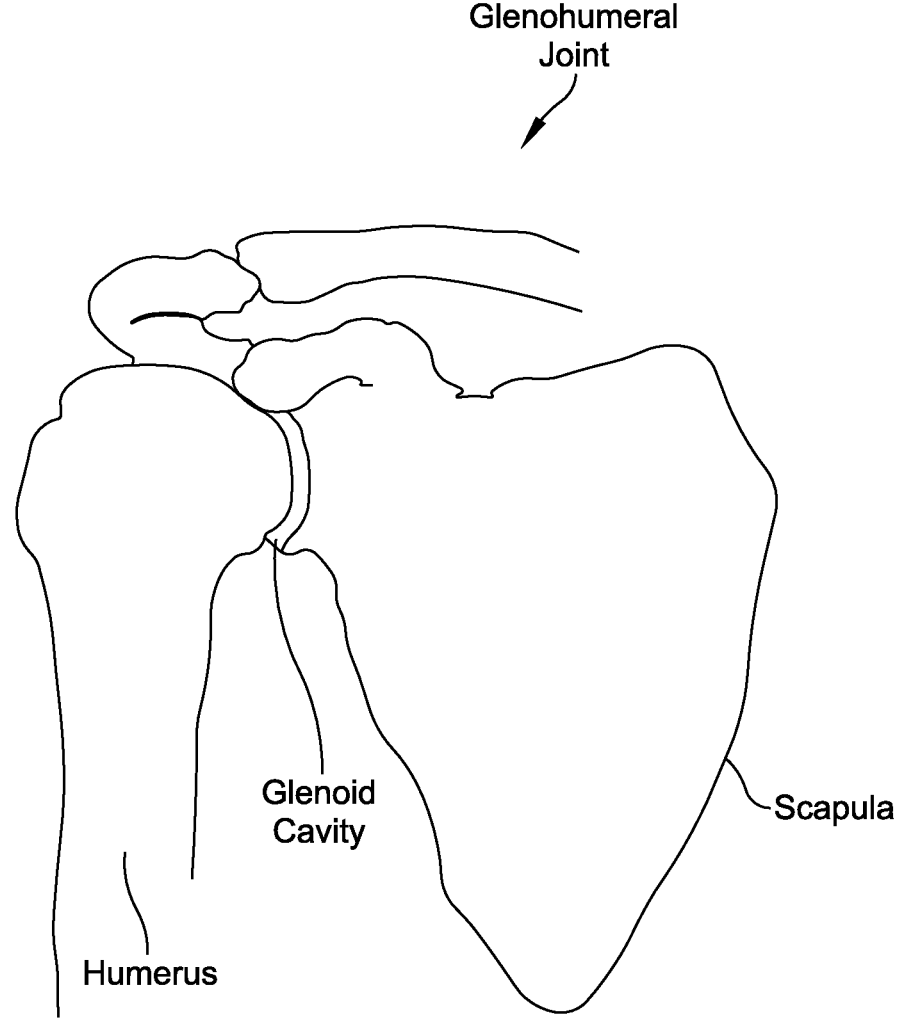
FIG. 1 is a schematic view of the human shoulder.

FIG. 1 depicts the human shoulder joint, which is sometimes called the glenohumeral joint. The glenoid cavity is an articular surface of the shoulder joint, which is located on the scapula. The glenoid cavity articulates with the humeral head to permit arm motion at the glenohumeral joint. Total shoulder arthroplasty replaces the articular surfaces of the glenohumeral joint with prosthetic articular surfaces that replicate the naturally occurring concave and convex surfaces of the body. Typically, in total shoulder arthroplasty, a humeral articular component is provided that has a surface that replaces the natural humeral head and a glenoid articular component is provided that has a surface that replaces cartilage in the glenoid cavity. In a typical reverse total shoulder arthroplasty, a glenoid articular component with a convex, e.g., spherical, configuration is coupled with the scapula at or in the glenoid cavity and a complimentary concave articular structure is placed on the humerus. Reverse total shoulder arthroplasty thus reverses the naturally occurring convexity and concavity orientation of the glenohumeral joint.

Figure 2:
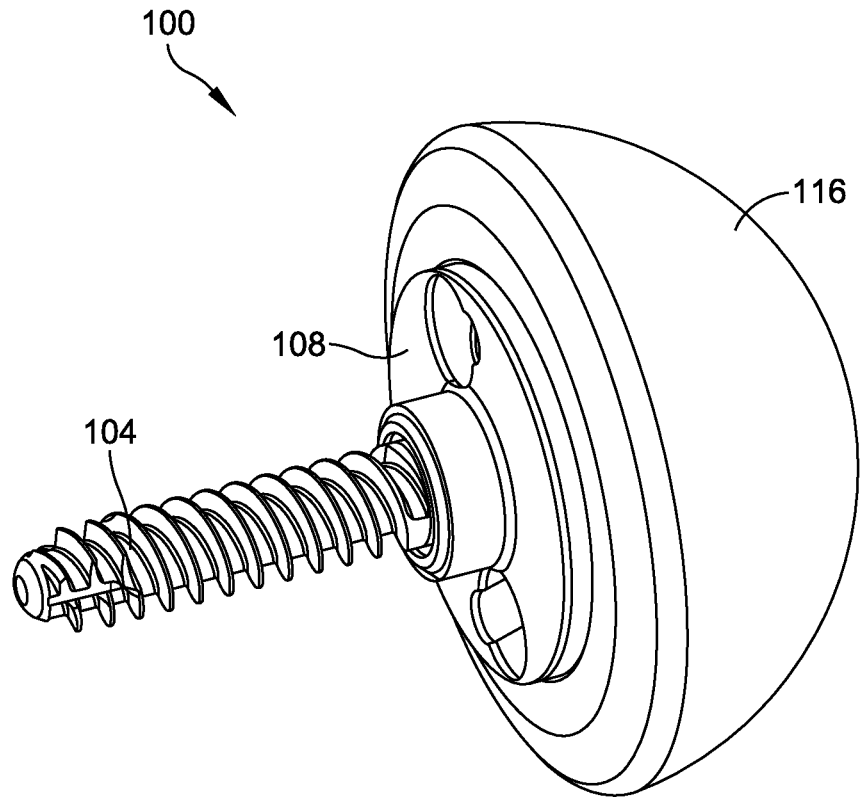
FIG. 2 is a perspective view of a glenoid implant in an assembled configuration.
Figure 3:
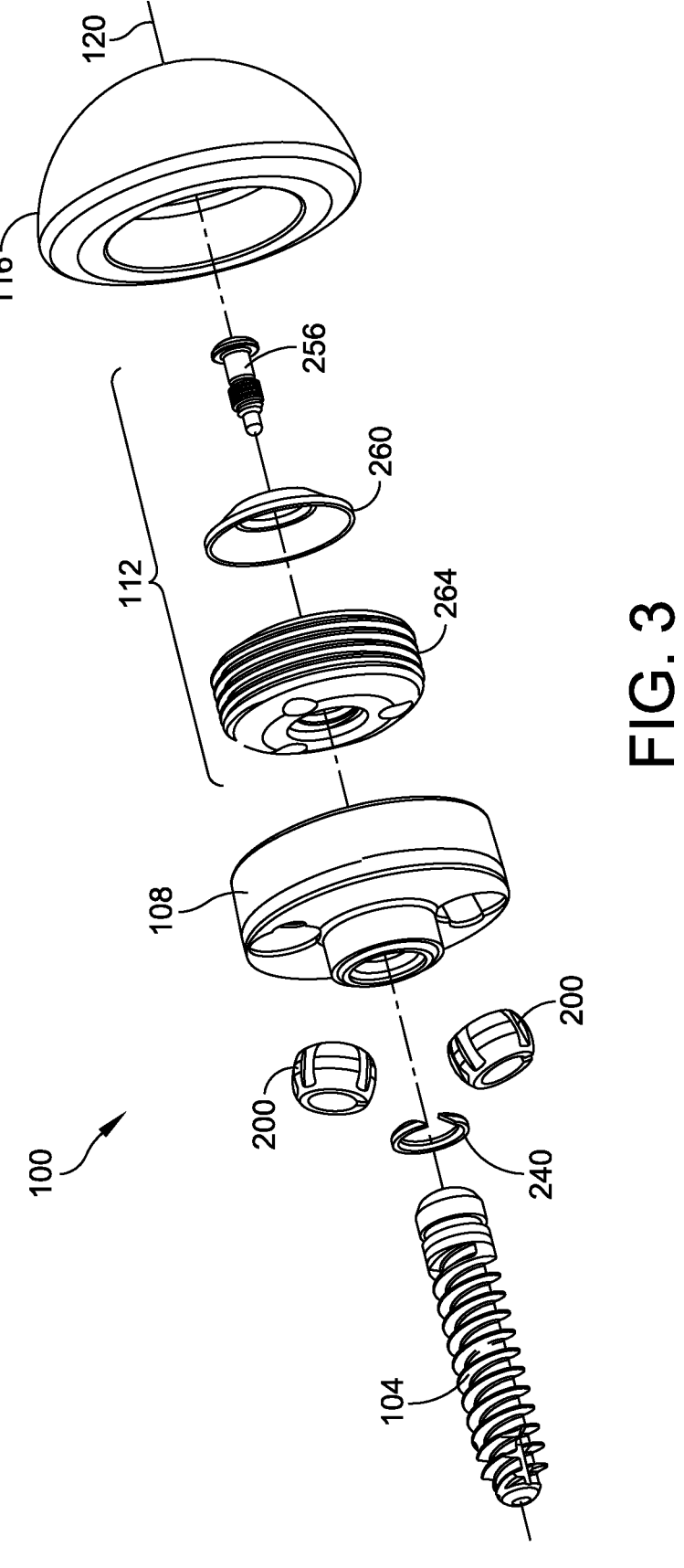
FIG. 3 is an exploded view of the glenoid implant shown in FIG. 2.
Figure 4:
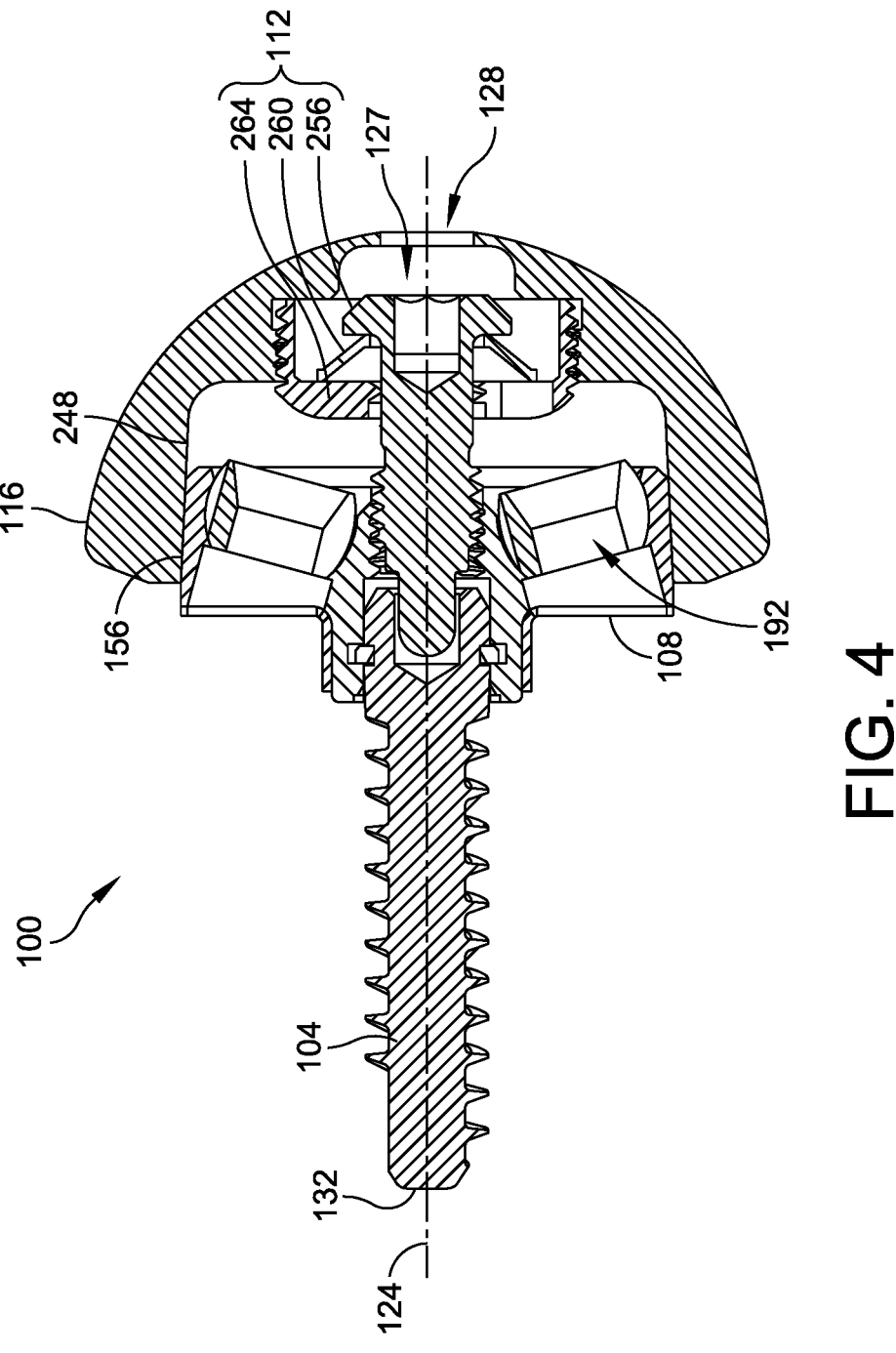
FIG. 4 is a cross-sectional side view of the glenoid implant shown in FIG. 2.

FIGS. 2-4 show an articular component assembly or implant 100 configured to be implanted in the glenoid cavity of a patient. The glenoid implant 100 includes an anchor member 104 for anchoring the implant 100 in the scapula, a baseplate 108, a locking structure 112 configured to deter rotation of the anchor member relative to the baseplate. The reverse glenoid implant assembly 100 also includes a glenosphere 116 providing a convex (e.g., spherical) articular surface. The glenosphere 116 is configured to couple to a concave surface of or on a humerus (not shown) to provide shoulder joint motion in the patient. The glenoid implant 100 and a corresponding humeral component provide a replacement for the natural glenohumeral joint.

As used herein, the terms "distal" and "proximal" are used to refer to the orientation of the glenoid implant as shown in FIG. 2-4. As shown in FIG. 3, a longitudinal axis 120 of the glenoid implant 100 extends through a central longitudinal axis 124 of anchor member 104 (shown in FIG. 4). The glenosphere 116 is towards the proximal end along the longitudinal axis 120 and the anchor member 104 is towards the distal end along the longitudinal axis 120. In other words, an element is proximal to another element if it is closer to a central aperture 128 (shown in FIG. 4) of the glenosphere 116 than the other element, and an element is distal to another element if it closer to a distal tip 132 (shown in FIG. 4) of the anchor member 104 than the other element. A cavity 127 of the glenosphere 116 is located immediately distal to the aperture 128. The cavity 127 can be considered to extend to a distal side of the glenosphere 116. At some points below, reference may be made to the anatomical location. In use when the implant is delivered into a patient's scapula, the distal tip 132 of the anchor member 104 is more medial on the patient, whereas the articular surface of the glenosphere 116 is more lateral on the patient.

Figure 5:
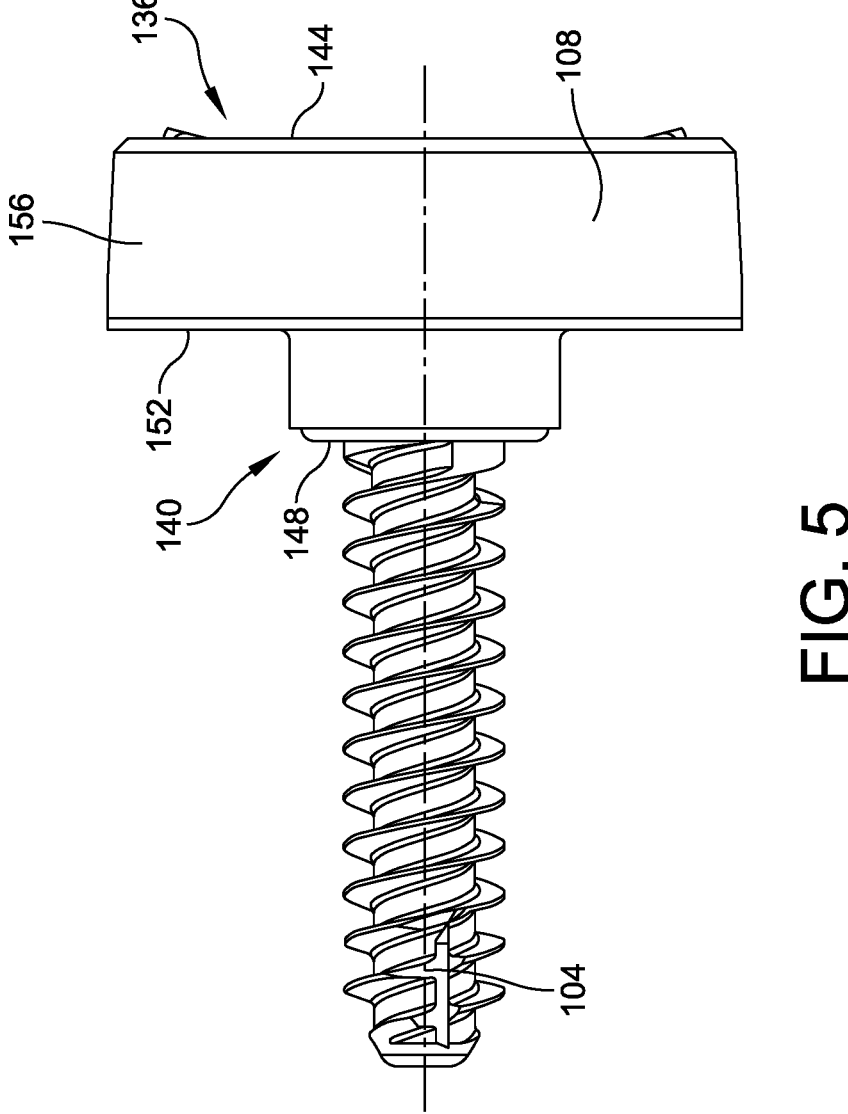
FIG. 5 is a side view of a baseplate and an anchor member of a glenoid implant.

FIGS. 3 and 4 show that the baseplate 108 is oriented substantially perpendicular to the longitudinal axis 120 of the glenoid implant 100. The baseplate 108 is shown coupled to the anchor member 104 in FIG. 4 and apart from the anchor member 104 in FIG. 5. The baseplate 108 also has a proximal end 136 and a distal end 140. The proximal end 136 comprises a proximal surface 144 and the distal end 140 comprises a distal surface 148. The proximal surface 144 can be substantially parallel to the distal surface 148. The baseplate 108 can also include a bone engaging surface 152. A thickness of the baseplate 108 defined between the proximal surface 144 and the bone engaging surface 152 may correspond to the amount that the baseplate 108 extends above a bone surface when implanted in the scapula. The thickness can be in a range between about 2 mm and about 12 mm, e.g., between about 4 mm and about 9 mm, e.g., about 6 mm. Thicknesses of about 3 mm, 5 mm, 7 mm, 8 mm, 10 mm and 11 mm are also contemplated. The bone engaging surface 152 can be lateralized in some embodiments. The bone engaging surface 152 can be substantially parallel to the proximal surface 144 and/or the distal surface 148. The bone engaging surface 152 can be angled, forming a wedge or other non-parallel structure. The bone engaging surface 152 can be patient specific.

The baseplate 108 also has a peripheral surface 156 that spans between the proximal surface 144 of the baseplate 108 and the bone engaging surface 152 of the baseplate 108. The surface 156 is disposed lateral with regard to the center of the implant 100 and also is disposed lateral of the mid-plane of the patient when the implant 100 is applied to the patient. The peripheral surface 156 can have a circular profile when viewed in a cross-section plane extending parallel to the proximal surface 144. The diameter of the circular profile can be between about 20 mm and about 40 mm, e.g., between about 25 mm and about 35 mm, e.g. about 30 mm. In some embodiments, the lateral surface 156 of the baseplate 108 is configured to form a portion of a friction lock engagement, such as a Morse taper. In one embodiment, the lateral surface 156 of the baseplate 108 is tronconical. The term tronconical, as used herein, refers to a shape or surface that is or is similar to a truncated cone. In some embodiments, the lateral surface 156 is configured with a gradually increasing perimeter in a direction from proximal surface 144 toward the bone engaging surface 152. The surface 156 is configured to mate with an interior surface 248 that is tapered or tronconical or otherwise configured to create high friction with the baseplate 108. Some, e.g., a majority of the thickness of the baseplate 108 can be received in the cavity 127 in some cases as the surfaces 156, 248 engage.

Figure 5A:
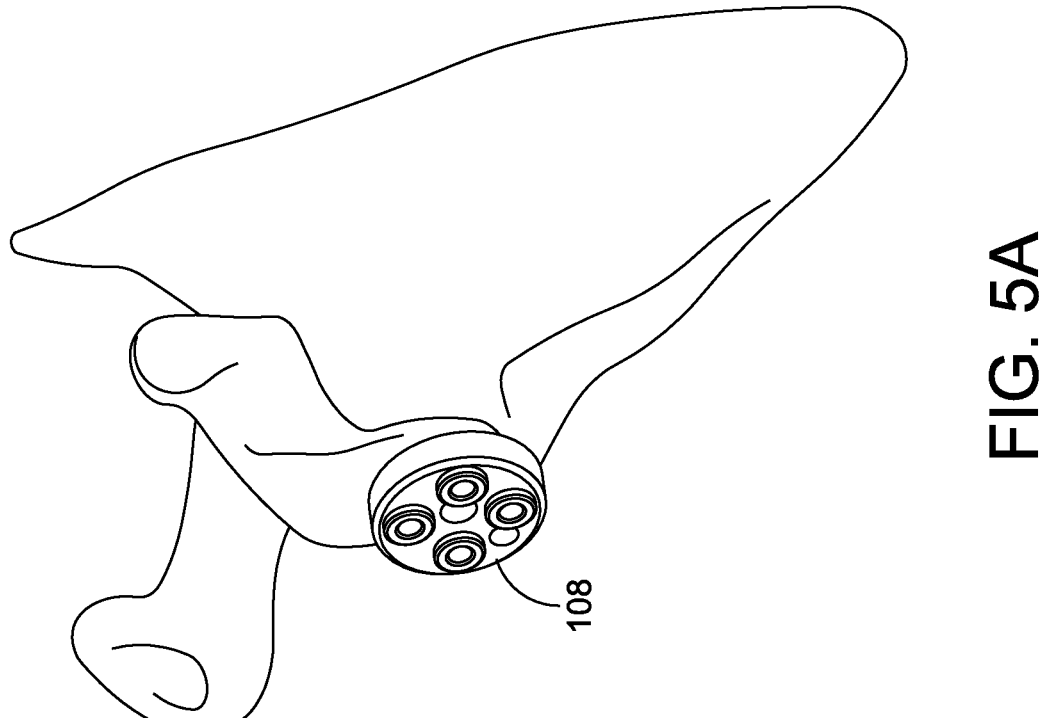
FIG. 5A shows a baseplate secured to a glenoid region of a scapula.
Figure 5B:
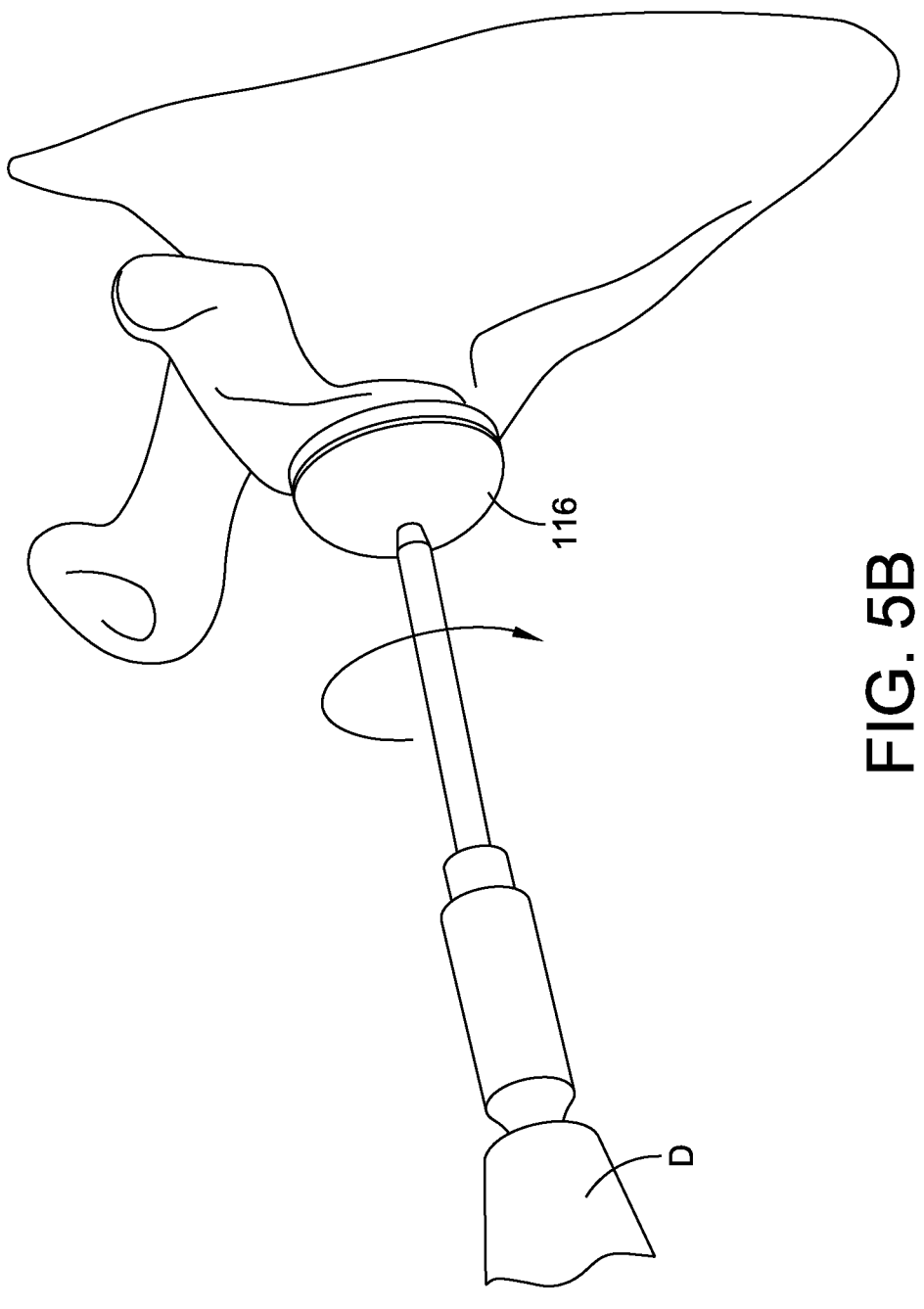
FIG. 5B shows a glenosphere attached to the baseplate at a glenoid region of a scapula.
Figure 6:
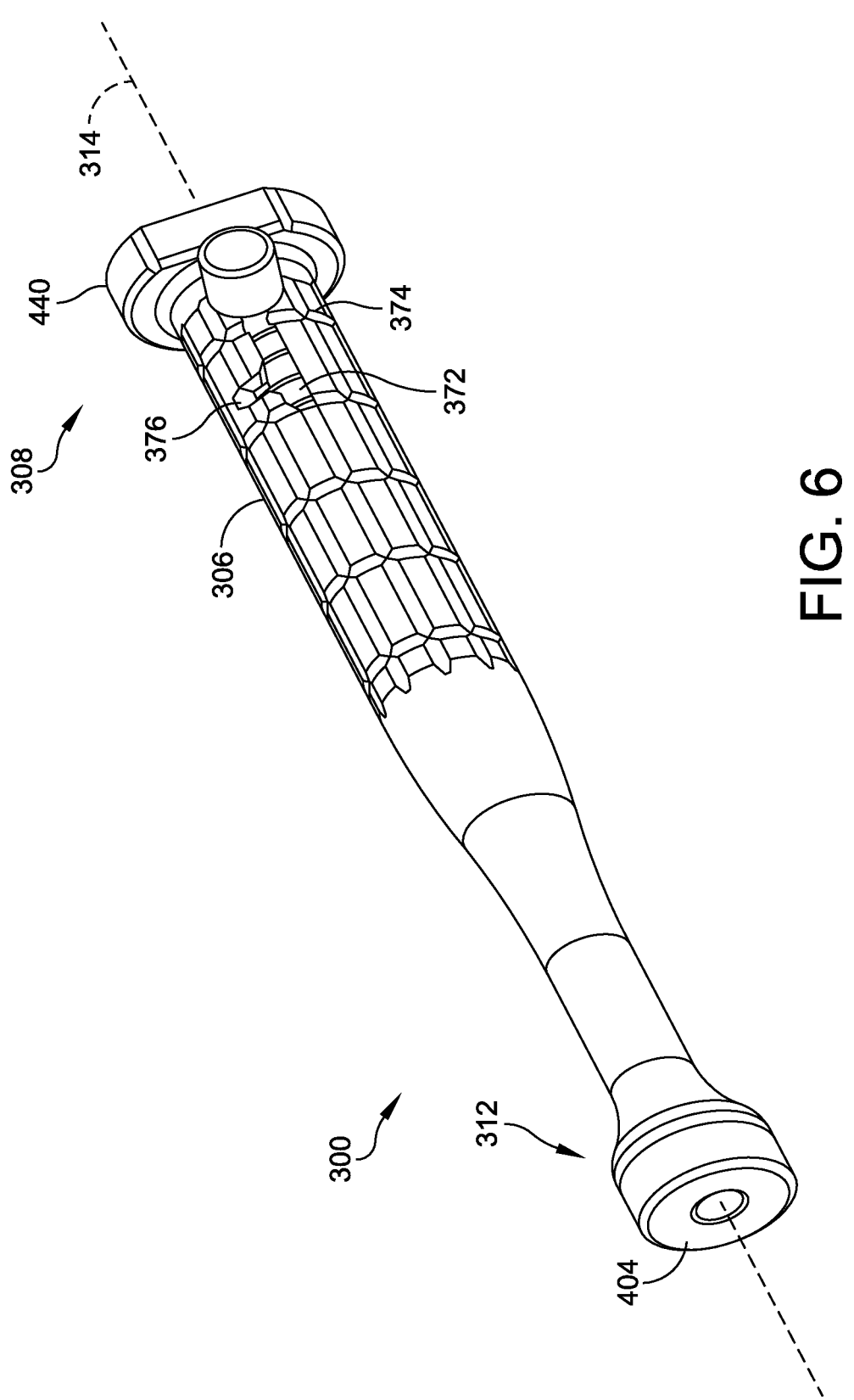
FIG. 6 is a perspective view of an impactor that can be used as a handling tool and can be used to impact a glenosphere onto a glenoid baseplate.

FIGS. 5A and 5B shows the baseplate 158 and the glenosphere 116 implanted in the scapula. The baseplate 158 can be secured to the scapula by the anchor member 104 and a plurality of screws that extend through peripheral holes 192 (e.g., one, two three, four or more than four such holes). The holes 192 can be formed through internal members that can swivel within the baseplate 108 to help direct the peripheral screws. After the baseplate 158 is secured to the scapula the glenosphere 116 can be attached thereto. The glenosphere 116 is placed against the baseplate 158. A handling tool such as those discussed below, which can optionally also be an impactor, can be used to engage the surfaces 156, 248 with each other initially. Thereafter a locking screw 256 can be advanced using a driver D (see FIG. 5B). In some embodiments, the locking screw 256 has a blind hole. In some embodiments, the locking screw 256 has a lumen from proximal end to distal end to allow access by a handling tool control member, such as the the impactor 300, the impactor 300A or the impactor 300B discussed further below. The locking screw 256 can be accessed through the central aperture 128 by traversing a proximal (or lateral) portion of the cavity 127 within the glenosphere 116. FIG. 4 illustrates how the advancement of the locking screw 256 can greatly enhance the frictional engagement between the internal surface 248 of the glenosphere 116 and the peripheral surface 156 of the baseplate 158. The locking screw 256 also secures the baseplate 108 against rotation that could cause the connection between the scapula and the reverse glenoid implant assembly 100 to be loosened. FIG. 3 shows how the locking screw 256 can be coupled with the glenosphere 116, e.g., through a compression washer 260 and a threaded member 264. The locking screw 256, compression washer 260 and the threaded member 264 can collectively be a locking structure 112. Other locking structures can be used to connect the locking screw 256 to the baseplate 108. Although the locking screw 256 is shown as solid with a blind recess on the proximal side, the screw 256 can be cannulated with a lumen extending all the way through the screw from a proximal end to a distal end.

FIG. 5B is illustrative of the manner of securing the glenosphere 116 to the baseplate 158 but in a patient the presence of soft tissue makes secure handling of the glenosphere 116 very important to a simpler and in some cases a more successful surgery. The impactors and handling tools discussed and claimed below facilitate such handling. After the glenosphere 116 is engaged with the scapula, an articular surface of a humeral assembly can be placed thereon to provide shoulder joint motion.

Figure 7:
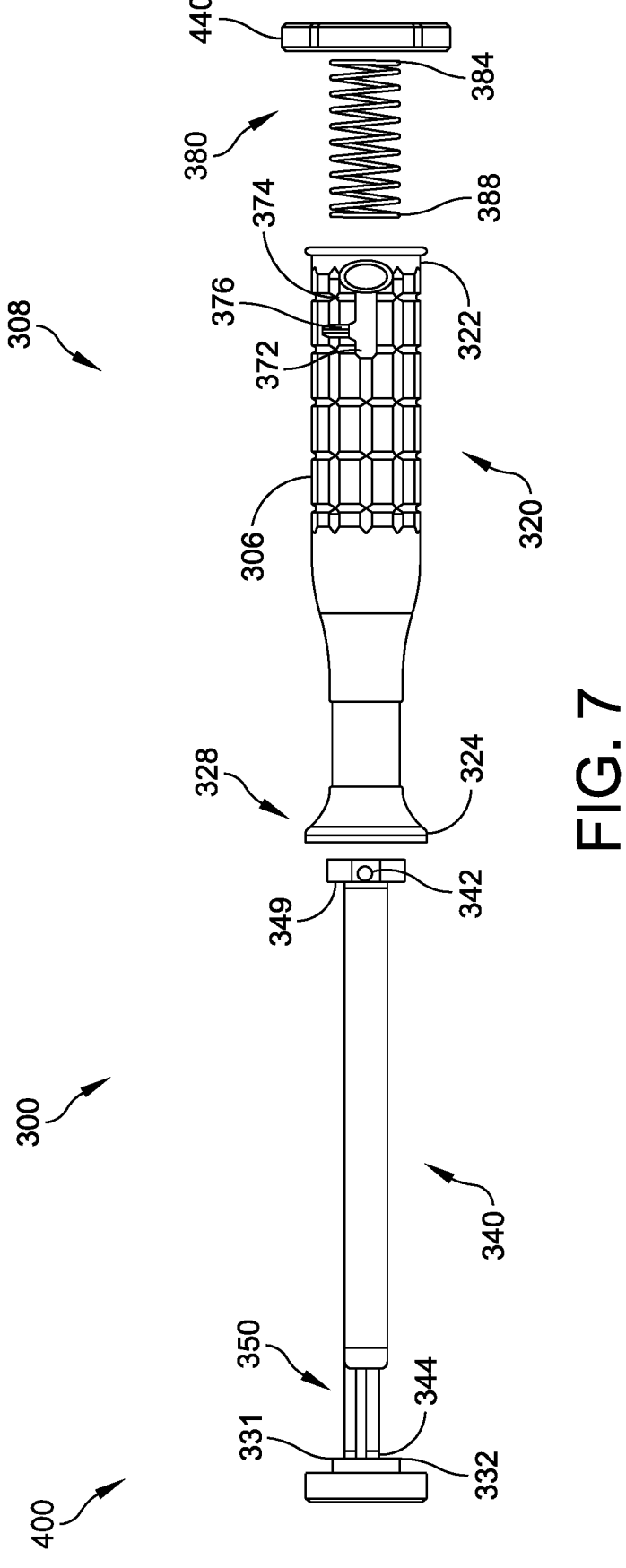
FIG. 7 is an exploded view of the impactor illustrated in FIG. 6.

FIG. 7 shows an impactor 300 that can be used for convenient handling of the glenosphere 116. The impactor 300 is one example of a handling tool disclosed herein. The impactor 300 can include a handle assembly 304 that includes a handle member 306 disposed at a proximal end 308 of the impactor 300. In the context of the impactor 300, "proximal" and the proximal direction is at or toward the handle member 306 and "distal" or the distal direction of the impactor 300 is toward an impaction tip 400 (discussed below). The impactor 300 includes a distal end 312. A longitudinal axis 314 extends along the impactor 300, including from the proximal end 308 to the distal end 312. The proximal end 308 provides for surgeon handling and for application of an impaction force or load, e.g., at a strike plate 440 (discussed below). The distal end 312 interfaces with the glenosphere 116, e.g., by engaging the glenosphere and retaining it against the impaction tip 400 in a hands free manner. For example, the impactor 300 can generate a proximally directed force against a glenosphere 116 to press the glenosphere against the impaction tip 400. The impaction tip 400 can provide a reaction force that holds the glenosphere 116 in place between the impaction tip 400 and a tip portion of the impactor 300 as discussed below.

The handle assembly 304 can include an outer elongate body 320 that extends from a proximal end 322 to a distal end 324 thereof. The outer elongate body 320 can include a lumen 326 that extends along the longitudinal axis 314 between the proximal end 322 and the distal end 324. The lumen 326 can vary in size with a smaller diameter portion for slideable support of a slender shaft of an inner elongate body 340 and a larger diameter portion for slideable support of an enlarged portion at the proximal end thereof. The larger diameter portion of the lumen 326 can also enable a spring or other compression member to be disposed therein between the outer elongate body 320 and the inner elongate body 340. The handle assembly 304 can include the strike plate 440. The strike plate 440 can be integrally formed with the outer elongate body 320. The strike plate 440 can be removeably mounted to the outer elongate body 320. The strike plate 440 can be configured to provide access to the lumen 326, as discussed further below.

The handle assembly 304 can include a distal portion 328 configured to couple with the impaction tip 400. The impaction tip 400 can be removeably mounted to the distal portion 328 of the outer elongate body 320. In one example, the distal portion 328 includes a concave distal opening 330 that is configured to receive a proximal projection 331 of the impaction tip 400. Engagement of the proximal projection 331 with the concave distal opening 330 can be by any suitable structure, such as threads 332. The proximal projection 331 can be connected with the concave distal opening 330 by a bayonet connection or by snap-fit, such as using a c-ring or other flexible connector.

In one example, the distal portion 328 of the outer elongate body 320 includes an enlarged outer profile. For example, the diameter of the distal end 324 of the outer elongate body 320 can be larger than an outer diameter of the outer elongate body 320 at a location proximal to the distal end 324. A mid-span of the outer elongate body 320 can be a reduced profile compared to the distal end 324. The mid-span of the outer elongate body 320 can be a reduced profile compared to the proximal end 322. The mid-span of the outer elongate body 320 can be a reduced profile compared to both the proximal end 322 and the distal end 324. A reduced profile mid-span can allow the impactor 300 to be inserted through a small incision in the area within the dashed box A (see FIG. 8). The impactor 300 can be widened at or toward the distal end 324 to provide good engagement with the glenosphere 116. The impactor 300 can be widened in a direction toward the proximal end 322 to enable the handle member 306 to be comfortably grasped by the surgeon. The side profile of the impactor 300 include a continuous concave curve as seen in FIGS. 7-10. The continuous concave curvature allows for moving soft tissue away from the impactor 300 in a less traumatic manner.

Figure 8:
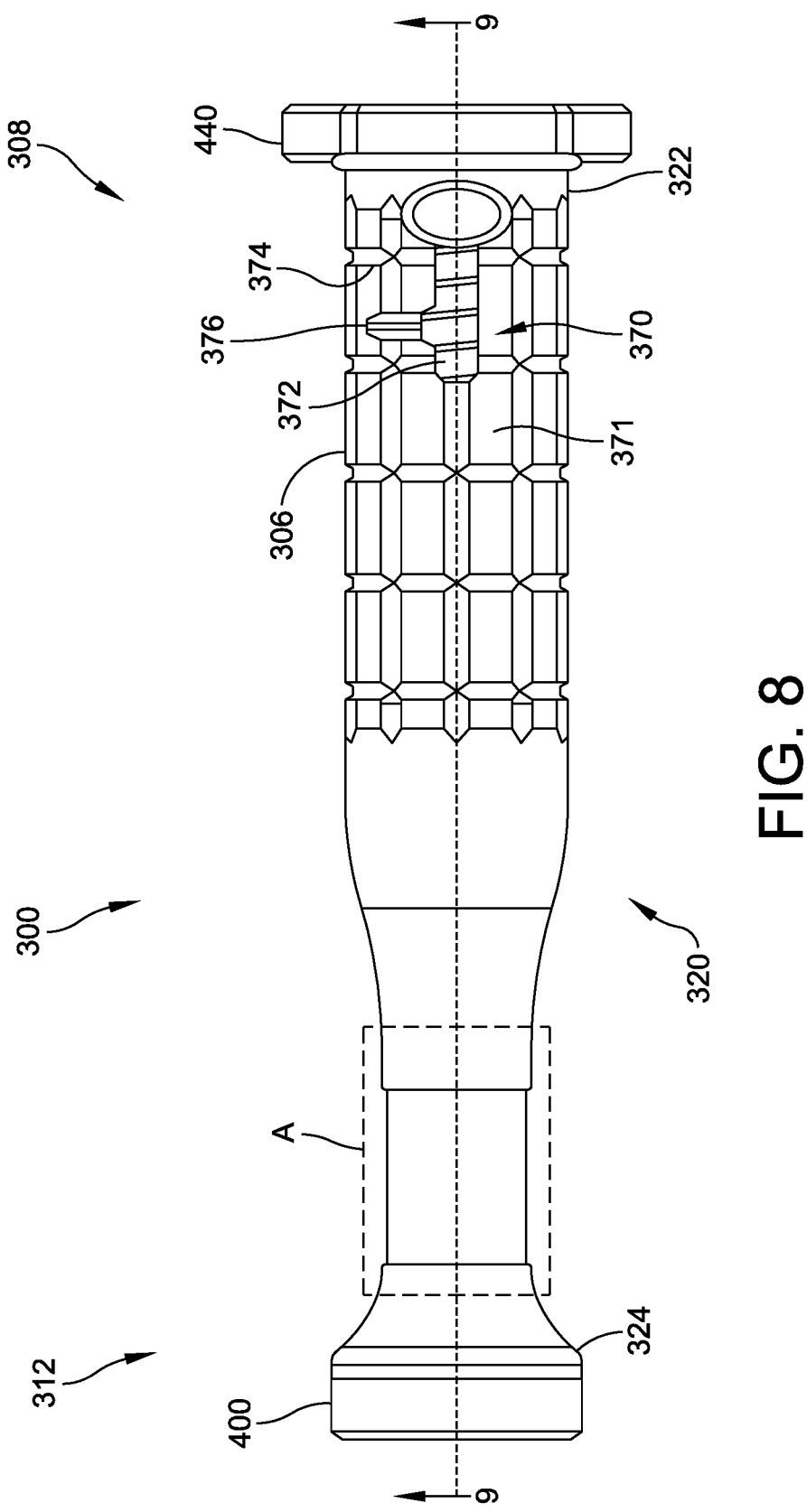
FIG. 8 is a side view showing an actuator configured to manipulate a retention portion disposed at a tip of the impactor of FIG. 6.
Figure 9:
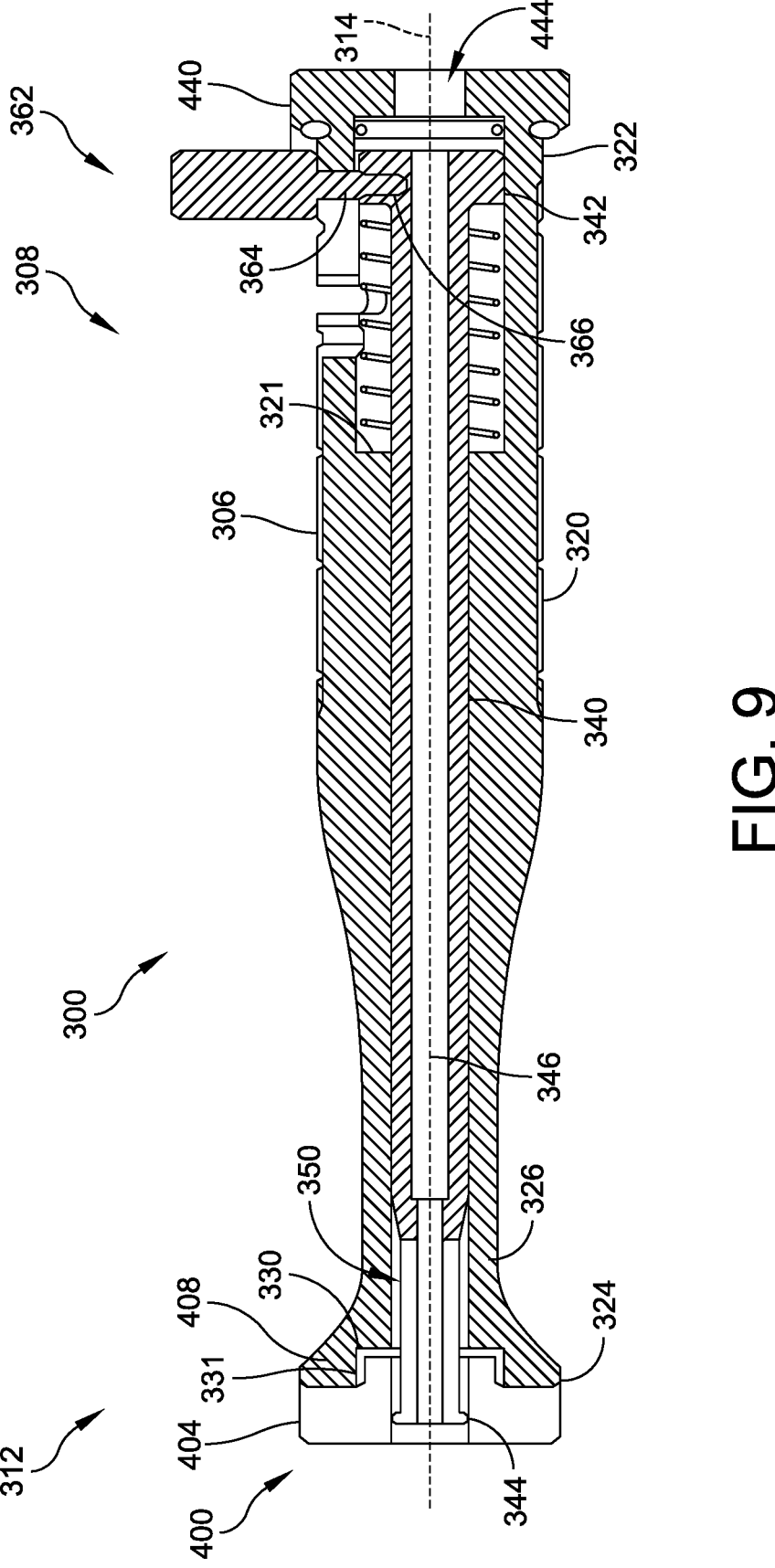
FIG. 9 is a cross-sectional view of the impactor of FIG. 6 taken at the section plane 9-9 shown in FIG. 8.

FIGS. 7-9 show that the impactor 300 can have an inner elongate body 340 which can comprise a unitary or monolithic body or can include an assembly. The inner elongate body 340 can include a proximal end 342 and a distal end 344. The inner elongate body 340 can include a lumen 346 extending therethrough, e.g., from the proximal end 342 to the distal end 344. The inner elongate body 340 can be centered on the longitudinal axis 314. The lumen 346 can be centered on the longitudinal axis 314. The lumen 346 can provide for direct access between the proximal end 308 to the distal end 312 of the impactor 300. The lumen 346 can be used to deliver a surgical wire or other control member, as discussed further below. A surgical wire is one example of a control member that can be separated from or can be separable from other components of the impactor 300. A variation of the impactor can include an integrated control member that can be moved to engage and disengaged the inner elongate body 340 with a glenosphere.

The inner elongate body 340 also can include an enlarged portion 348 at or adjacent to the proximal end 342. The enlarged portion 348 can include a distal facing surface 349. The outer elongate body 320 can include a proximal facing surface 321 disposed therein, e.g., within the region of the handle member 306. An enlarged portion of the lumen 326 within the region of the handle member 306 can allow the enlarged portion 348 to slide therein. The enlarged portion can extend proximally from the proximal facing surface 321 of the outer elongate body 320.

In some cases, the position of the enlarged portion 348 is at least partially controlled by operation of a compression spring 380 or other spring member. The compression spring 380 or other spring or resilient member can be configured to apply a traction force (e.g., a proximally oriented force) to the inner elongate body 340, e.g., to the distal facing surface 349. The compression spring 380 can be compressed between the proximal facing surface 321 of the outer elongate body 320 and the distal facing surface 349 of the inner elongate body 340. When the enlarged portion 348 is moved forward, the distal facing surface 349 acts on a first end 384 of the compression spring 380 to move the first end 384 of the compression spring 380 and to compress the spring against the proximal facing surface 321 of the outer elongate body 320. The proximal facing surface 321 is in contact with a second end 388 of the compression spring 380. The results is the storing of strain energy in the compression spring 380 which can be released as the compression spring 380 is restored upon moving the enlarged portion 348 and the rest of the inner elongate body 340 proximally within the lumen 326 of the outer elongate body 320. The traction force can be applied by the inner elongate body 340 to the glenosphere 116 and toward the handle member 306 when the glenosphere is coupled with the inner elongate body 340, e.g., is coupled with a deflectable tip portion 350 disposed at the distal end 344 thereof.

The lumen 346 can provide access to a space 352 in the vicinity of the deflectable tip portion 350. In one example, the space 352 allows the deflectable tip portion 350 to deflect when the space 352 is not occupied. Deflection of the deflectable tip portion 350 is restricted, reduced or eliminated when the space 352 is occupied. The space 352 can comprise a distal portion of the lumen 346, e.g., can be an area within the impactor 300 that is aligned with the lumen 346 along the longitudinal axis 314. The space 352 can be accessed by advancing a control member or device through an aperture 444 strike plate 440. The aperture 444 can be aligned with the lumen 346 to provide access from the strike plate 440 to the distal end 344 of the inner elongate body 340. As discussed further below, the aperture 444 and the lumen 346 can be configured to receive a surgical wire 460 (or other control member) to occupy or leave open the space 352 to control the deflection of the deflectable tip portion 350 in various phases of use of the impactor 300.

As noted above, the inner elongate body 340 is moveable within the lumen 326 of the outer elongate body 320. A device can be provided to facilitate this movement. For example, an actuator 362 can be provided that can be accessed from outside the outer elongate body 320 to move the inner elongate body 340 between multiple positions or along a range of positions. The actuator 362 can include an inner portion 364 that extends through the outer elongate body 320 and into the lumen 326. The inner portion 364 can extend to an inner end 366 engaged with the inner elongate body 340, e.g., with the enlarged portion 348. The inner end 366 can be a threaded end that can be threaded into a threaded hole in the enlarged portion 348. The inner end 366 can be secured to the enlarged portion 348 by other techniques, such as adhesive or interference fit. The actuator 362 can include an outer end 368 that is configured for finger actuation. The outer end 368 can include a profile that is enlarged compared to the inner portion 364. The outer end 368 can include a knurled surface to enhance finger gripping in use.

The impactor 300 can have a control feature to provide clear, tactile indications of the position of the actuator 362. The indication of the position of the actuator 362 can indicate to the user the position or state of the deflectable tip portion 350 which can be used to grip, hold or retain the glenosphere 116. In one example a slot 370 is provided in a side surface 371 of the outer elongate body 320. The slot 370 can be elongate in a direction corresponding to the longitudinal axis 314 of the impactor 300. The slot 370 can have a width in a direction transverse to the elongate direction of the slot 370 that is wide enough to allow the actuator 362 to pass therethrough. The slot 370 can have a first position 372 and a second position 374 disposed proximally, e.g., proximal of the first position 372, along the longitudinal axis 314 of the impactor 300. For example, the slot 370 can have an elongate oval configuration in which the first position 372 is at a distal end of the oval and in which the second position 374 is at a proximal end of the oval. The slot 370 can have a third position 376 disposed longitudinally between the first position 372 and the second position 374. The third position 376 can be circumferentially displaced from the first position 372, the second position 374. The third position 376 can be circumferentially offset from the slot 370 or another track disposed between the positions 372, 374. The third position 376 can provide a hands-free spring loaded position, e.g., where the deflectable tip portion 350 is extended to engage a glenosphere 116. The inner elongate body 340 can be released from the third position 376 toward the second position 374 after engaging the glenosphere 116 to draw the glenosphere into engagement with an impaction tip 400, as discussed further below.

Although the impactor 300 is shown with one circumferentially displaced position, e.g., the third position 376, there can be provided a plurality of circumferentially off-set positions corresponding to different degrees of extension of the deflectable tip portion 350 from the tip of the outer elongate body 320. If more than one circumferentially offset position is provided, one can be circumferentially off-set in a first direction and another can be provided in a second direction different from, e.g., opposite of, the first direction.

As will be discussed in greater detail below, the positions 372, 374, 376 provide different control positions of the impactor 300. In one example, the first position 372 is the most fully advanced position of the actuator 362 of the impactor 300. When the actuator 362 is in the first position 372 the distal portion 328 is fully extended from the impaction tip 400 of the impactor 300. The movement of the actuator 362 to the first position 372 causes the enlarged portion 348 of the inner elongate body 340 to move distally. Such movement moves the distal facing surface 349 toward the proximal facing surface 321 within the lumen 326. This movement causes the compression spring 380 to be compressed between the proximal facing surface 321 of the outer elongate body 320 and the distal facing surface 349 of the inner elongate body 340. The actuator 362 can be moved from the first position 372 to the third position 376. When in the third position 376 some but not all of the strain energy stored in the compression spring 380 is released. However, the remaining strain energy in the compression spring 380 provides an on-going traction load toward the proximal end 308 of the impactor 300. Before or after delivery of the glenosphere, the actuator 362 can be placed in the second position 374 in which the strain energy that may be stored in the compression spring 380 can be substantially released upon movement of the enlarged portion 348 and the rest of the inner elongate body 340 toward the proximal end 308 of the impactor 300.

In one embodiment an inner impactor assembly 382 can be provided that includes the inner elongate body 340, the deflectable tip portion 350, and the enlarged portion 348. These components can be integrally formed, e.g., as a monolith. Some or all of these components can be separate components that can be assembled together.

In some embodiments an outer impactor assembly 442 can be provided that includes the outer elongate body 320, the handle member 304, and the impaction tip 400. The outer impactor assembly 442 can include the strike plate 440 in some embodiments.

The impaction tip 400 can include a distal portion 404 and a proximal portion. The distal portion 404 can be flat or can have a curvature configured to match one or more sizes of the glenosphere 116.

Figure 10:
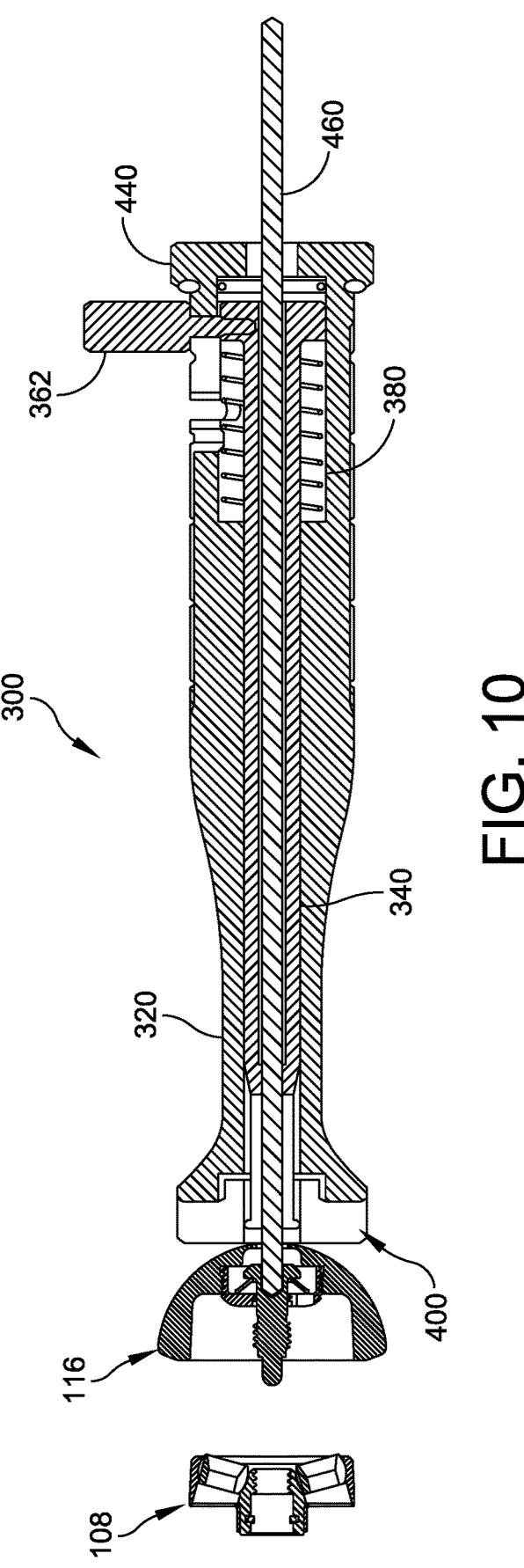
FIG. 10 is a cross-sectional view similar to that of FIG. 9 illustrating how a glenosphere component can be held at a distal portion of the impactor of FIG. 6.
Figure 10A:
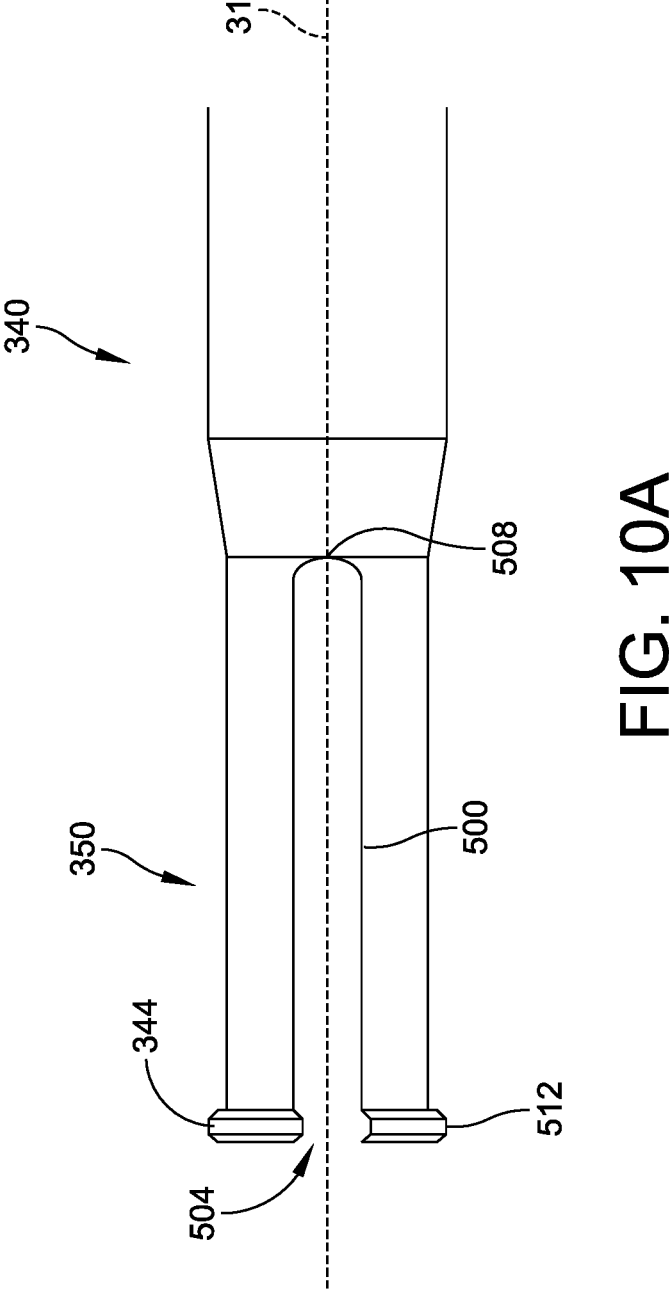
FIG. 10A is a side view of a deflectable tip that can provide a retention portion to a handling too, such as the impactor of FIG. 6.
Figure 10B:
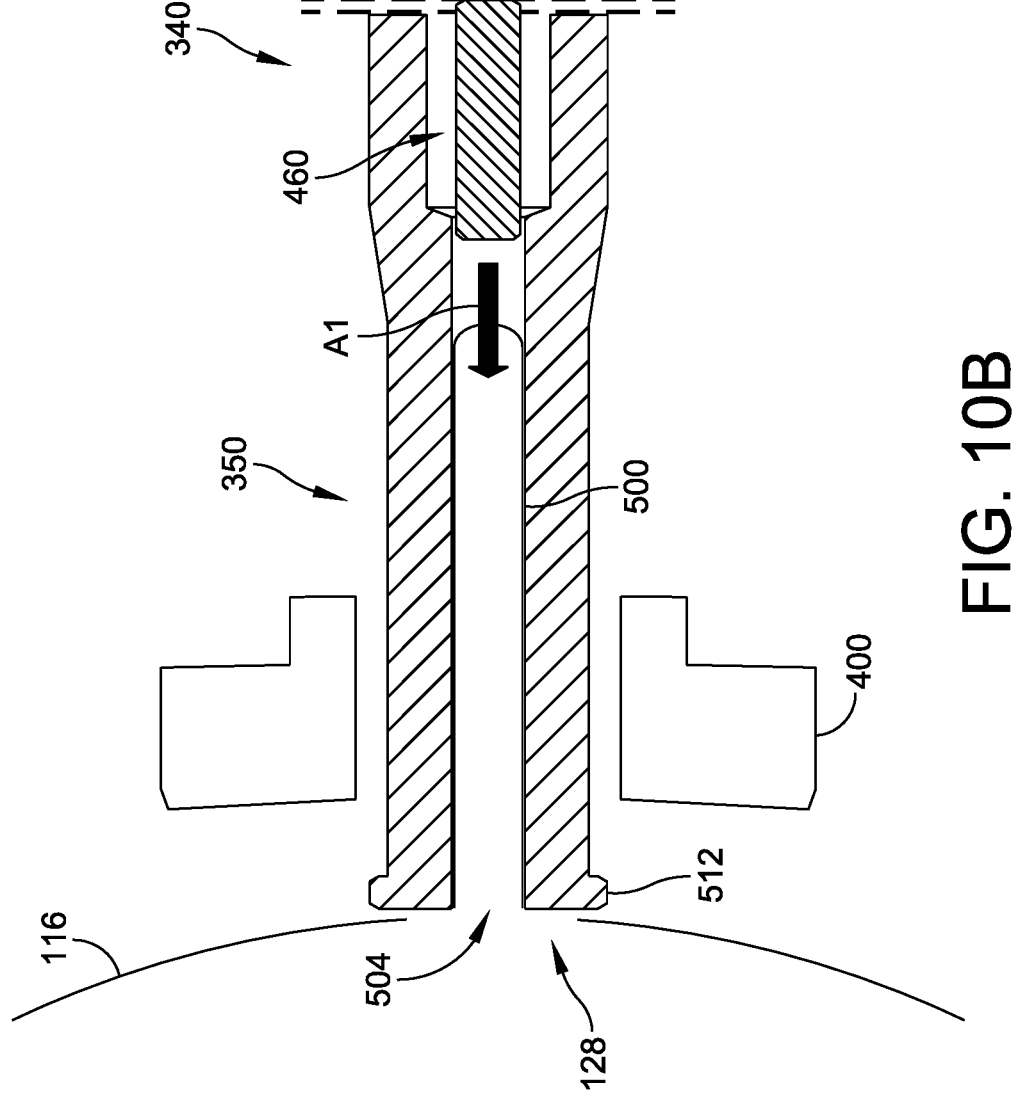
FIG. 10B is schematic showing a cross-section of the deflectable tip portion of the impactor of FIG. 6 with a distal portion of a surgical wire disposed proximal thereto and a distal end thereof being disposed adjacent to a glenosphere.
Figure 10C:
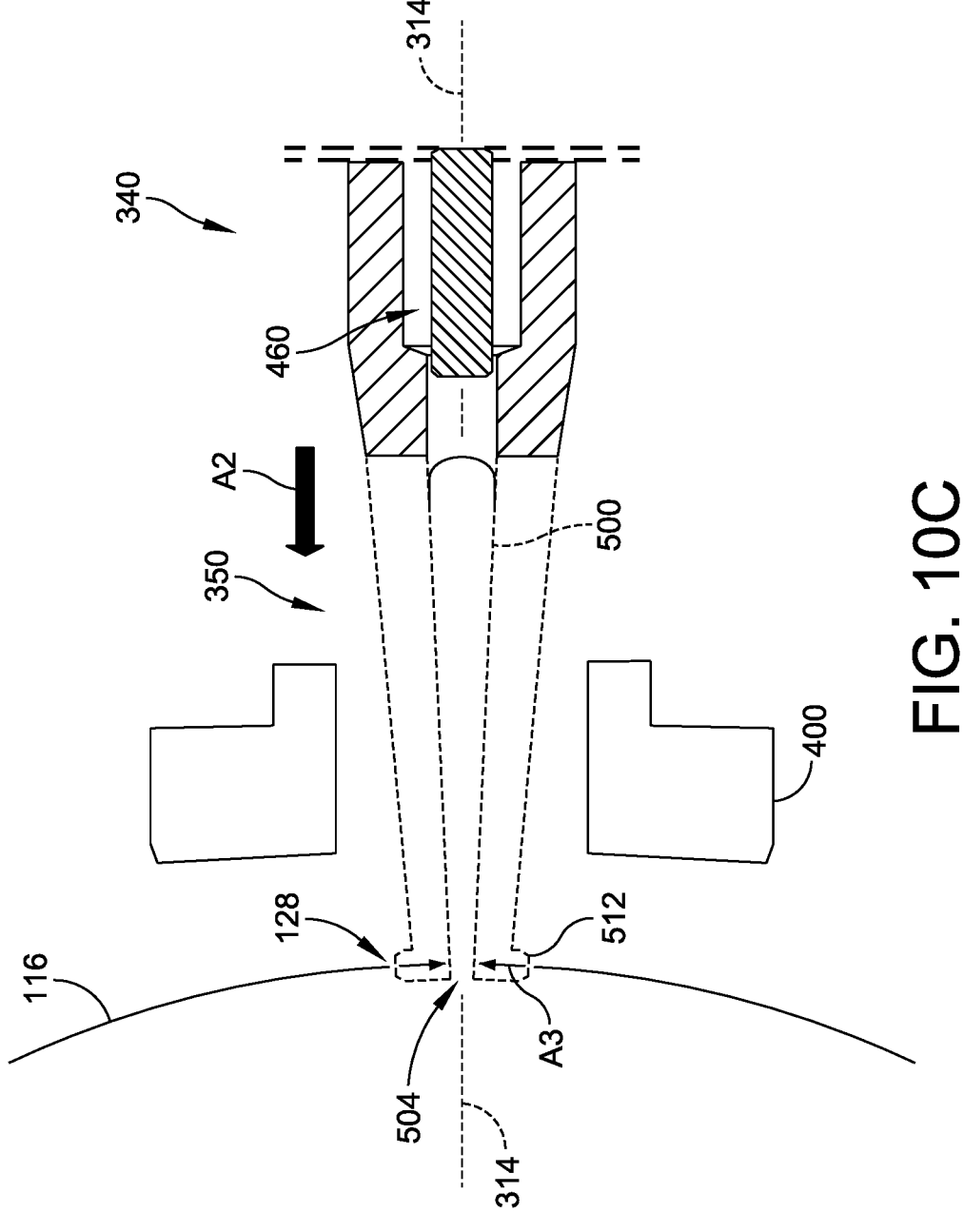
FIG. 10C shows deflection of the tip portion of the impactor of FIG. 6 following engagement of the tip portion with an opening in the glenosphere.
Figure 10D:
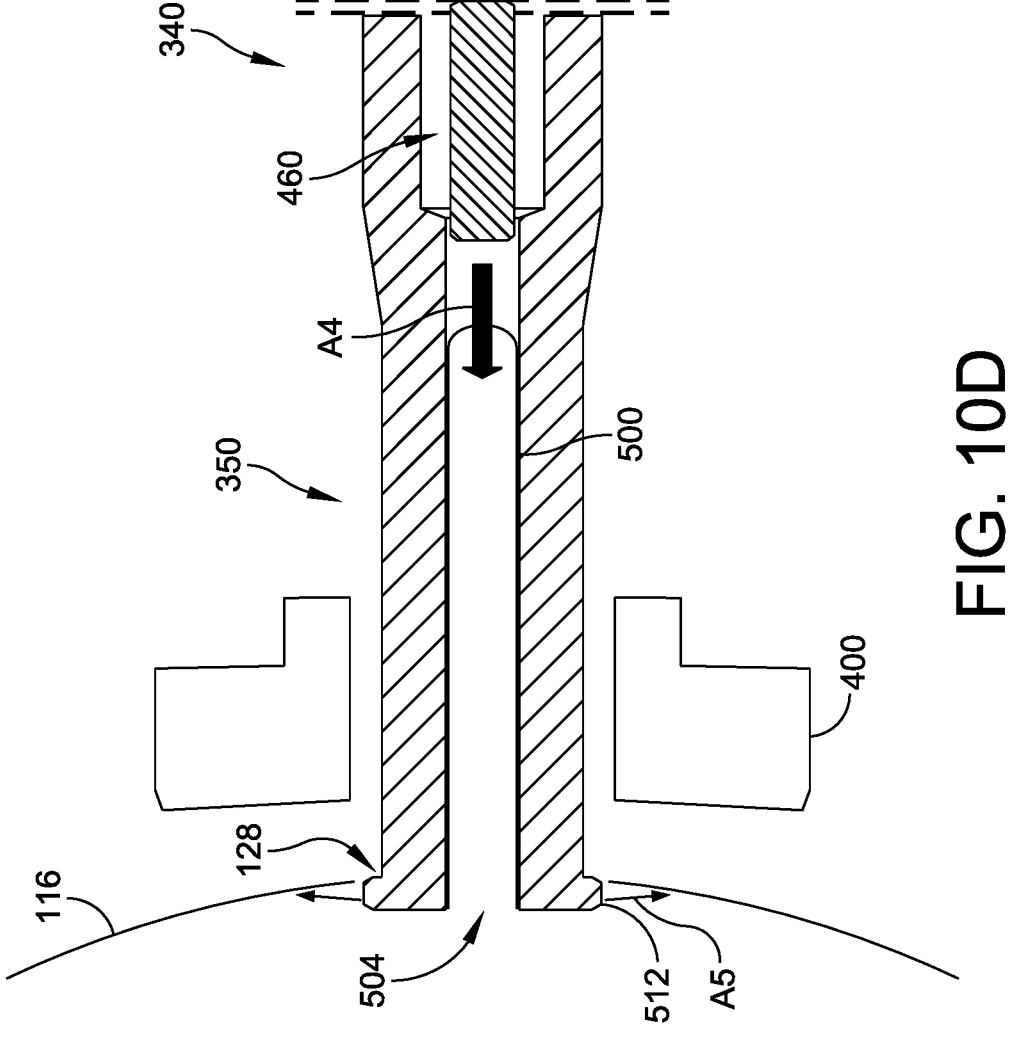
FIG. 10D shows restoration of (e.g., expansion of) at least some of the deflection of the tip portion of the impactor of FIG. 6 following advancement of the tip portion through the opening in the glenosphere.
Figure 10E:
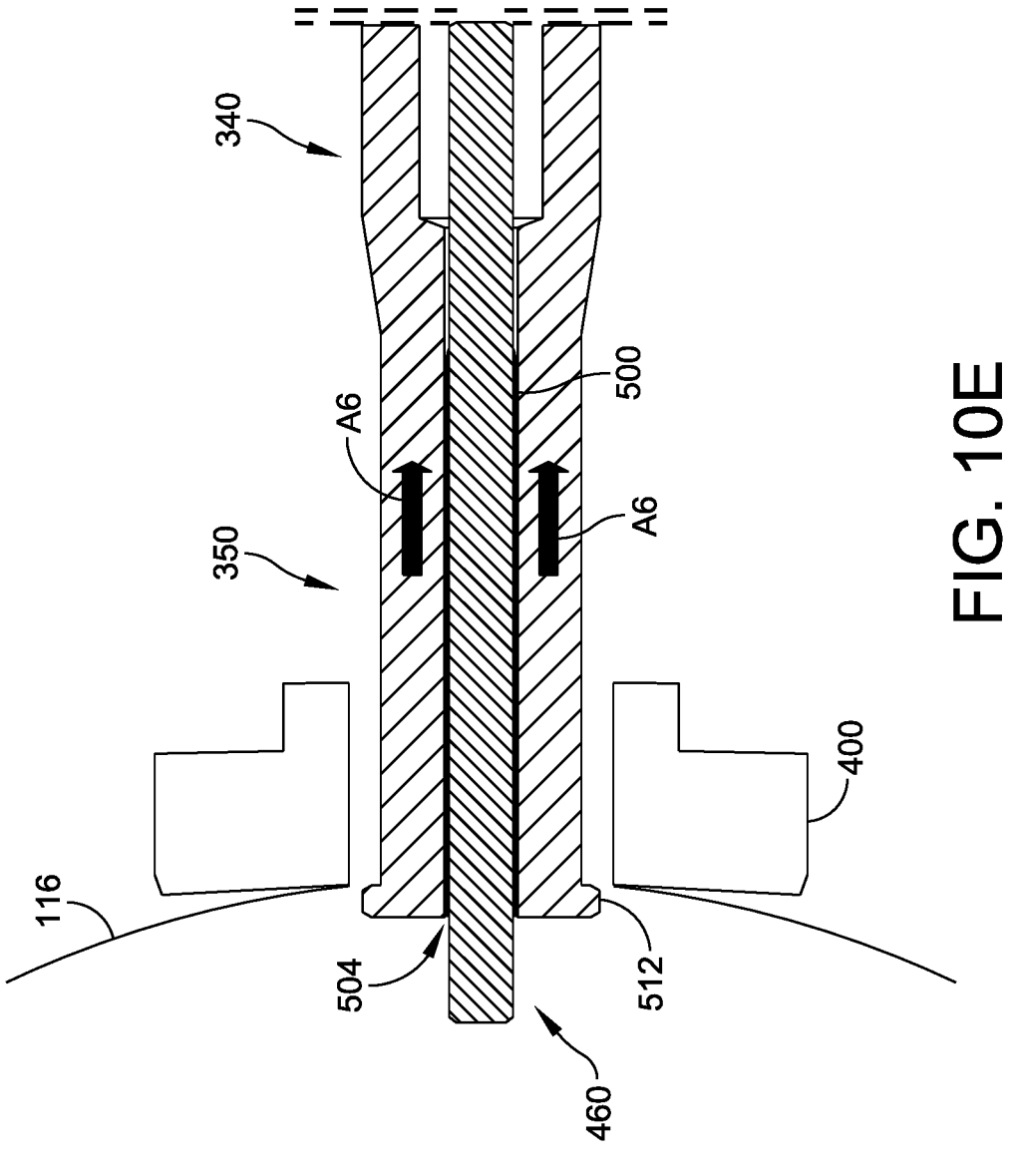
FIG. 10E shows the surgical wire positioned in or distal to the deflectable tip portion and an impaction tip of the impactor of FIG. 6 engaged with a glenosphere.
Figure 10F:
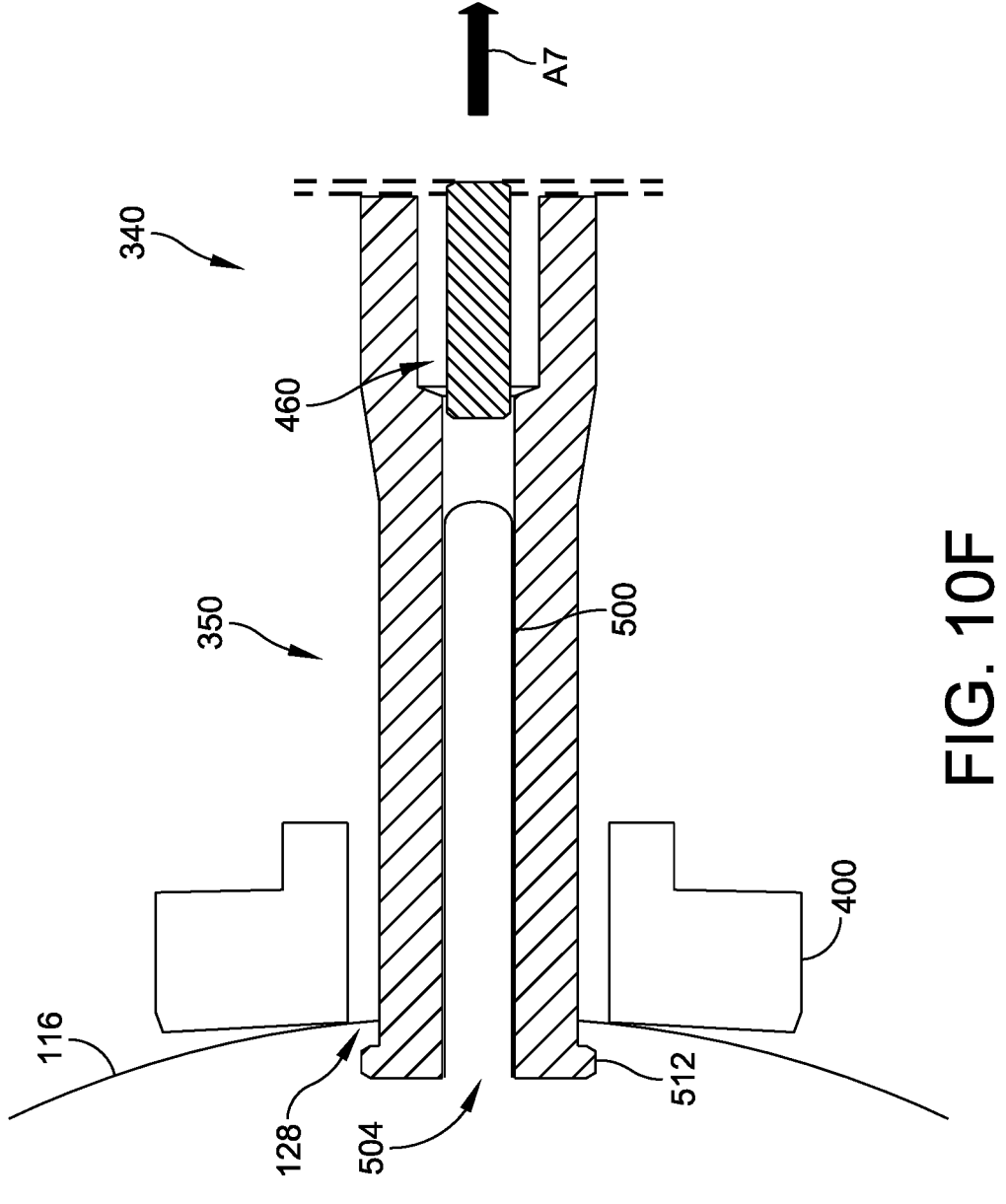
FIG. 10F shows the surgical wire withdrawn out of the deflectable tip portion of the impactor of FIG. 6, just prior to impaction.

FIGS. 10-10F show the impactor 300 and how it can be used as a handling tool to handle and to deliver a glenosphere 116 to a baseplate mounted to a glenoid surface. FIG. 10 shows components of the impactor 300 assembled and the impactor in a configuration for holding the glenosphere 116. FIG. 10 also shows a baseplate 108 that would be implanted separately (see FIG. 5A). The baseplate 108 can be secured to the scapula using the anchor 104 and one or more peripheral screws, or by other techniques. The glenosphere 116 can be temporarily but securely retained by the impactor 300 in methods illustrated in FIGS. 10A-10F.

Figure 11:
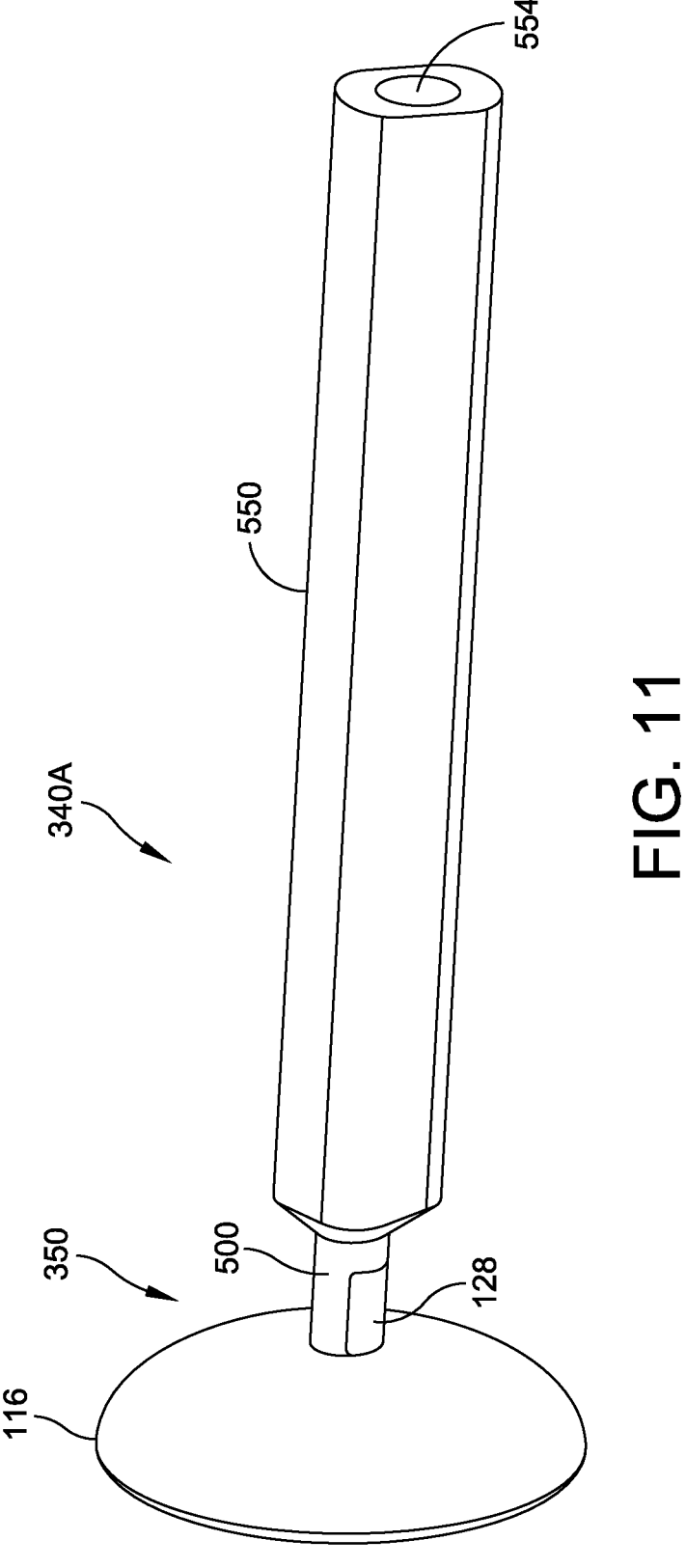
FIG. 11 shows an embodiment of a handling tool that includes an elongate body that can be combined with and/or separable from an outer elongate body or other impaction load delivering structure.
Figure 12:
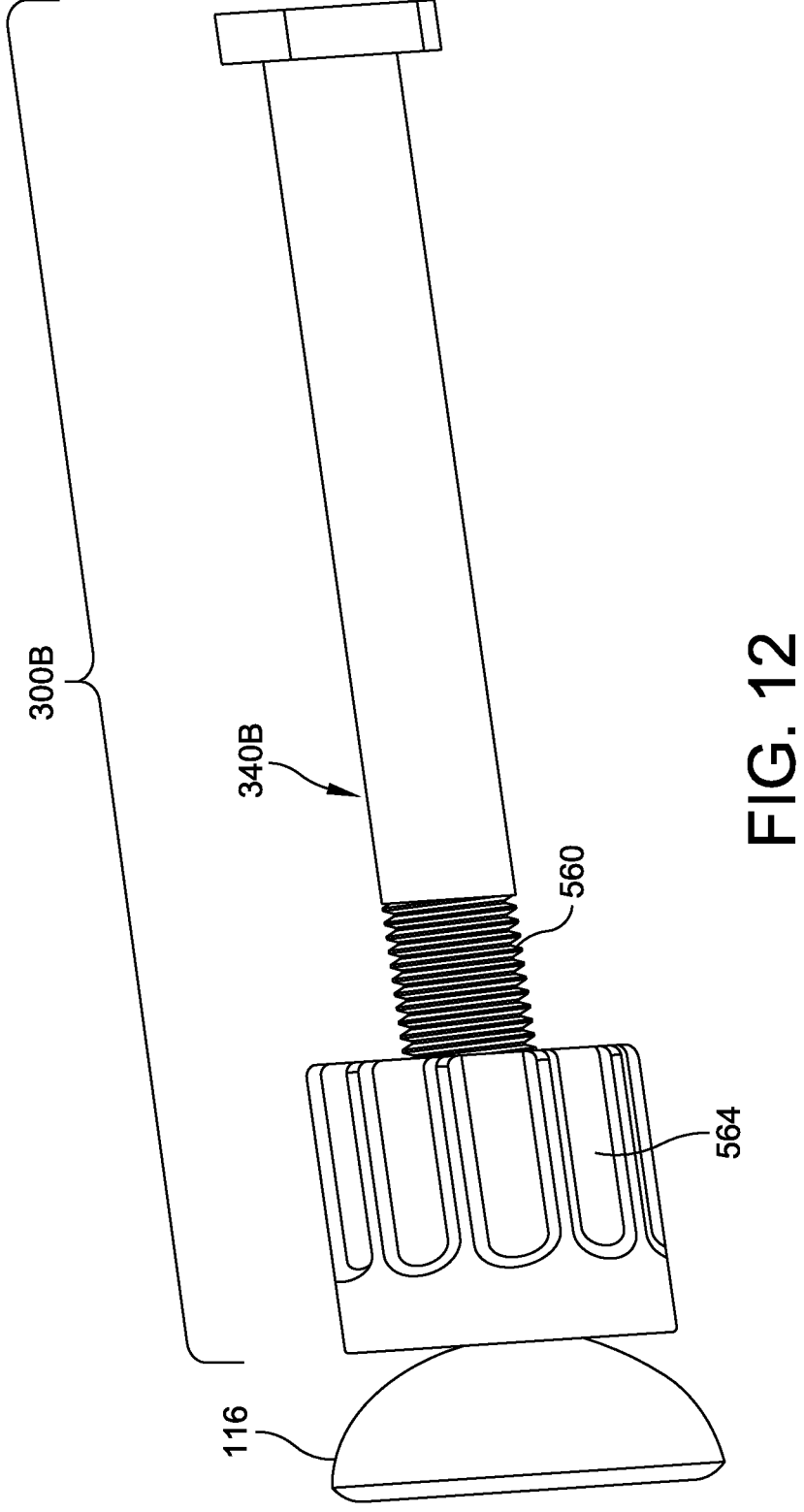
FIG. 12 shows another embodiment of a handling tool that can include a separator that is coupled with a threaded surface of an elongate body to disengage a glenosphere from the elongate body.

FIG. 10A shows a partial view of a distal portion of the inner elongate body 340. Although the discussion of the use of the inner elongate body 340 in these methods is in the context of the impactor 300, the elongate body is present in other handling tools that may not include the outer elongate body 320, e.g., as shown in FIGS. 11-12. However, some aspects of these methods also apply to the embodiments of FIGS. 11-12. The inner elongate body 340 has a deflectable tip portion 350 that is adjacent to, e.g., extending proximally from a distal end 344 of the inner elongate body 340. The deflectable tip portion 350 can have any suitable structure to make it flexible. For example, the deflectable tip portion 350 can include one or more, e.g., two slots 500. FIG. 10A shows that the slot(s) 500 can extend from a distal end 504 to a proximal end 508 of the slot(s) within the deflectable tip portion 350. The slot(s) 500 allow the distal end 504 to be deflected toward the longitudinal axis 314 of the impactor 300. The proximal end 508 can include a radius portion, e.g., a rounding to facilitate the resilient deflection of distal end 504.

The deflectable tip portion 350 can include an enlarged portion 512 disposed at the distal end 344. The enlarged portion 512 can be used to deflect the deflectable tip portion 350 as discussed in greater detail below. The profile, e.g., diameter, of the deflectable tip portion 350 can vary from that of a portion of the inner elongate body 340 disposed proximally of the deflectable tip portion 350. For example, the inner elongate body 340 can have an outer diameter in a proximal section and in a tapered portion between the proximal section and the deflectable tip portion 350. The portion of the deflectable tip portion 350 along the slot 500, e.g., between the proximal end 508 and the enlarged portion 512 can have a smaller diameter than that of the tapered portion of the inner elongate body 340. The smaller diameter of the deflectable tip portion 350 provides clearance between the deflectable tip portion 350 and the inner periphery of the central aperture 128 of the glenosphere 116. The clearance can allow the deflectable tip portion 350 to slide within the aperture 128 in an undeflected or minimally deflected state.

FIG. 10B shows the deflectable tip portion 350 of the inner elongate body 340 and also shows the impaction tip 400 schematically. The outer elongate body 320 and other components of the outer impactor assembly 442, which can include the handle member 304 and the strike plate 440, have been removed to simplify the drawing. But these components generally are present as discussed further below. The enlarged portion 512 of the deflectable tip portion 350 can be advanced relative to the impaction tip 400 such that the enlarged portion 512 is exposed at the distal end 312 of the impactor 300. This can be achieved by any suitable approach, such as by advancing the actuator 362 within the slot 370 to or toward the first position 372. As the actuator 362 is moved toward the first position 372 of the slot 370 the enlarged portion 512 can be sufficiently advanced relative to a distal face of the impaction tip 400 to allow the enlarged portion 512 to engage the glenosphere 116. For example, the distal face of the enlarged portion 512 can be advanced toward the surface of the glenosphere 116 around the aperture 128. The open status of the lumen 346 in the vicinity of the deflectable tip portion 350 allows the tip portion to be deflected.

The actuator 362 can be positioned within the slot 370 to a position in which it is held in place, or locked. Such a position can be any in which the surgeon need not continue to hold the actuator 362 and yet the inner elongate body 340 is advanced relative to the outer elongate body 320. As discussed above, some embodiments can have a compression spring 380 that stores strain energy when the inner elongate body 340 is advanced. Accordingly a force may be needed to hold the actuator 362 in a distal position corresponding to the position inner elongate body 340 shown in FIG. 10B. For example, the actuator 362 can be shifted circumferentially into the third position 376 such that a circumferential surface of the slot 370 can apply a force opposing the spring force of the compression spring 380. This allows the surgeon to release the actuator 362 and to focus on other aspects of the method of impacting the glenosphere 116.

In one technique, an arrow A1 shows movement of a surgical wire 460 in the lumen 346 to a location proximal to the deflectable tip portion 350. A distal end of the surgical wire 460 can be placed just proximal to the proximal end 508 of the slot 500, in one example. With the surgical wire disposed adjacent to the deflectable tip portion 350 the surgical wire 460 can be ready to be moved to a position within or distal to the deflectable tip portion 350.

FIG. 10C shows an arrow A2 corresponding to a distally directed movement or force applied to the impactor 300 upon contacting the enlarged portion 512 with the surface of the glenosphere 116 around the aperture 128. The movement of force corresponding to arrow A2 causes the distal end 504 at, within and proximal to the enlarged portion 512 to be deflected toward the longitudinal axis 314. The deflection of the enlarged portion 512 can be facilitated by an angled or chamfered surface at the distal face of the enlarged portion 512. The movement of the enlarged portion 512 is shown by an arrow A3. The arrow A3 shows a load being applied to the enlarged portion 512. The load can result in strain energy being stored in the deflectable tip portion 350. The strain energy can be stored until the enlarged portion 512 is disposed distal of the aperture 128 and within a cavity (see FIG. 4) within the glenosphere 116.

FIG. 10D shows a restoring of the deflectable tip portion 350 toward an undeflected position or configuration. An arrow A5 shows the movement of the deflectable tip portion 350 corresponding to strain energy being released from the deflectable tip portion 350. As noted above, the undeflected state or configuration of the deflectable tip portion 350 can result when the enlarged portion 512 is disposed beyond (e.g., distal to) the aperture 128 of the glenosphere 116. In this position the portion of the deflectable tip portion 350 with the smaller diameter is aligned with the aperture 128. There can be a clearance provided that allows the deflectable tip portion 350 to be fully undeflect. In some embodiments, the clearance can be minimal or negative such that when the enlarged portion 512 is disposed within the cavity of the glenosphere 116 the deflectable tip portion 350 is somewhat deflected toward the longitudinal axis 314.

FIG. 10D shows an arrow A4 that corresponds to moving the surgical wire 460 distally within the lumen 326 of the outer elongate body 320. The movement of the surgical wire 460 according to the arrow A4 can include shifting a distal end of the surgical wire 460 from proximal to the proximal end 508 of the slot 500 to a location at or distal to the enlarged portion 512. If the clearance between the outer diameter of the deflectable tip portion 350 proximal of the enlarged portion 512 and the surface of the glenosphere 116 around the aperture 128 is negligible or negative, e.g., the deflectable tip portion 350 is somewhat deflected when the enlarged portion 512 is in the cavity of the glenosphere 116 then the advancement of the surgical wire 460 may result in some compression of the outer surface of the deflectable tip portion 350 adjacent to the enlarged portion 512 and as a result a gripping of the periphery of the aperture 128.

FIG. 10E shows the surgical wire 460 fully advanced through the enlarged portion 512 to a position within the cavity of the glenosphere 116. FIG. 10 shows that the distal end of the surgical wire 460 can be distal to an assembly including the glenosphere 116. For example, the distal end of the surgical wire 460 can extend through the deflectable tip portion 350, the compression washer 260 and the threaded member 264 which retains the compression washer in the interior of the glenosphere 116. The surgical wire 460 can even be inserted into the locking screw when it is pre-assembled in the glenosphere 116. The surgical wire 460 can be advanced into a blind hole or a lumen that extends from a proximal end to a distal end of the locking screw 256.

In an advanced position or configuration, the surgeon can control the glenosphere 116 from the proximal end 308 of the impactor 300, e.g., by grasping the actuator 362 handle member 306. In one step between what is shown in FIGS. 10D and 10E the surgical wire 460 may be advanced distally as in FIG. 10E but the impaction tip 400 may be spaced proximally from the glenosphere 116 as in FIG. 10D. To move the impaction tip 400 into contact with the convex surface of the glenosphere 116, the actuator 362 can be moved out of the third position 376 of the slot 370 and can be allowed to return toward the second position 374 of the slot. The movement from the third position 376 to the second position 374 can result in a motion indicated by an arrow A6 resulting in the gap between a distal surface of the impaction tip 400 and the convex articular surface of the glenosphere 116 shown in FIG. 10D being closed such that there is contact between these surfaces, as shown in FIG. 10E. The compression spring 380 can release strain energy such that the closing of the gap can be automatic, e.g., without any continued movement by the surgeon. Of course, the impactor 300 could be configured without a spring such that the movement of the actuator 362 could be by surgeon finger action in another embodiment. Providing a release of strain energy from the compression spring 380 can result in a continued force (also in the direction of the arrow A6) being applied at the interface between the distal surface of the impaction tip 400 and the convex articular surface of the glenosphere 116, which can provide positive control of the position, location and orientation of the glenosphere 116 while the glenosphere 116 is engaged with the inner elongate body 340 and the actuator 362 is in the third position 376 of the slot 370.

The control provided in the configuration of FIG. 10E allows the surgeon to move the glenosphere 116 through an incision in the patient skin toward the baseplate 108 and onto the baseplate which has been placed on or adjacent to the glenoid (see FIG. 5A). The glenosphere 116 can be placed on the baseplate 108 such that mating tapered surface 156 of the baseplate 108 and 248 of the glenosphere 116 can be contacting each other. Initially, these tapered surfaces loosely contact each other and the surgeon can remove or reposition the glenosphere 116 on the baseplate 108 or even remove a first glenosphere 116 and place another one, e.g., of a different size.

FIG. 10F shows that the surgical wire 460 can be removed as indicated by an arrow A6 just prior to initially securing the glenosphere 116 to the baseplate 108. In this position the surgeon can maintain the initial contact between the tapered surfaces of the baseplate 108 and the glenosphere 116 by applying a distally (or medially) directed force through the outer elongate body 320 and the impaction tip 400 to the convex surface of the glenosphere 116. Once the surgical wire 460 has been withdrawn from the deflectable tip portion 350 the impactor 300 can be impacted at the strike plate 440. The surgical wire 460 can be fully withdrawn from the impactor 300, e.g., out of the aperture 444 thereof.

Figure 10G:
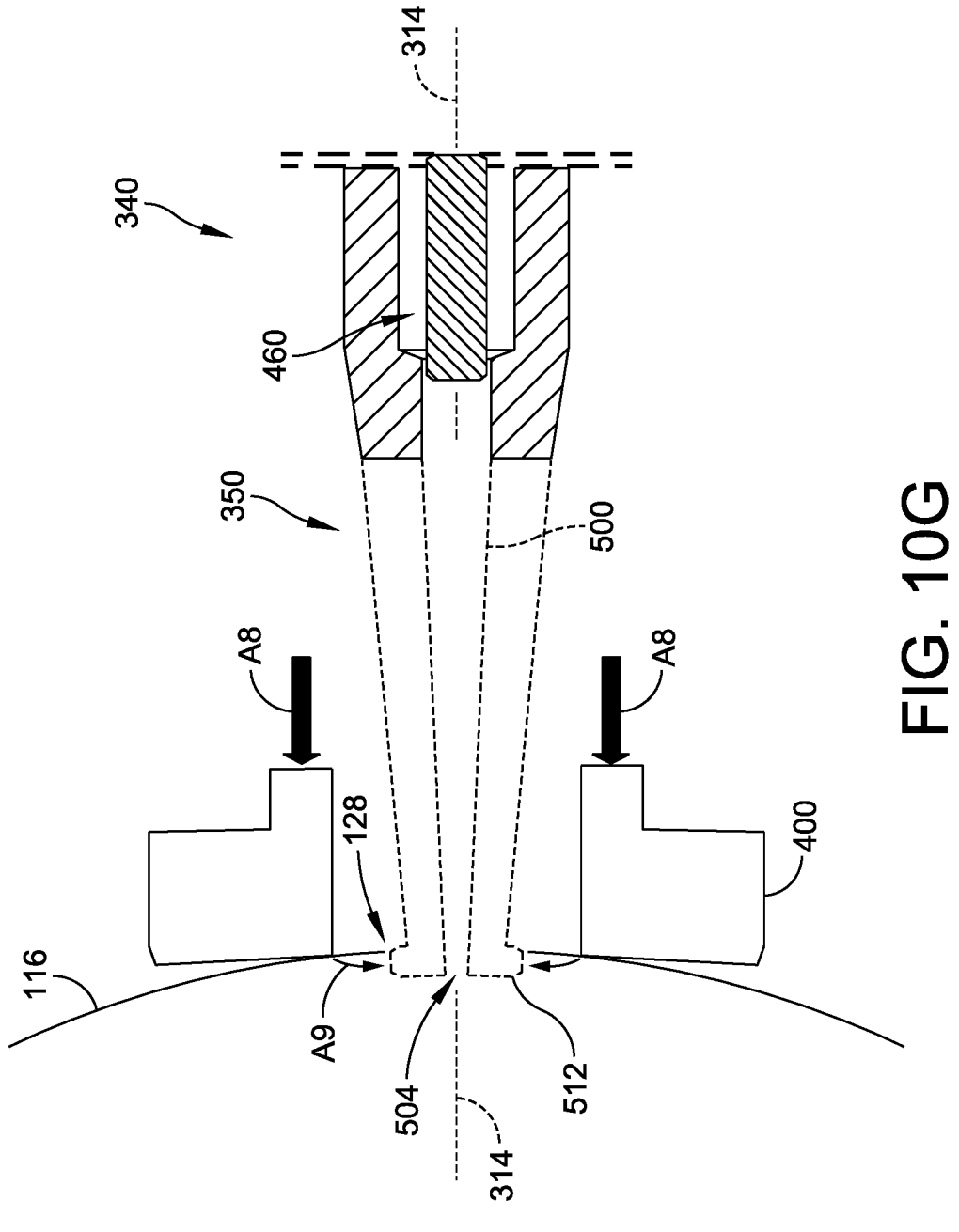
FIG. 10G illustrates how the impactor of FIG. 6 applies an impaction load to the glenosphere to couple the glenosphere to a baseplate.

FIG. 10G shows the application of an impaction force by an arrow A8. The force applied by the arrow A8 can be by an impactor striking the strike plate 440. The force can be conveyed through the outer elongate body 320 to the impaction tip 400. As discussed above, the inner elongate body 340 is slideable within the outer elongate body 320. The slideable coupling and the compression spring 380 substantially isolate the inner elongate body 340 from the load applied to the strike plate 440. As a result, there can be some distal displacement of the impaction tip 400 relative to the enlarged portion 512 upon application of the impaction force. In some cases, an impaction load on the strike plate 440 can simultaneously engage a glenosphere with a glenoid baseplate and disengage the retention portion from the glenosphere. The movement is facilitated by the length of the slot 370 in the side surface 371 of the handle member 306 and the travel of the actuator 362 therein. As the impaction tip 400 moves relative to the enlarged portion 512 the deflectable tip portion 350 is allowed to deflect toward the longitudinal axis 314 as indicated by an arrow A9. The deflection toward the longitudinal axis 314 decreases the profile of the enlarged portion 512 such that it is smaller than the aperture 128 of the glenosphere 116.

Figure 10H:
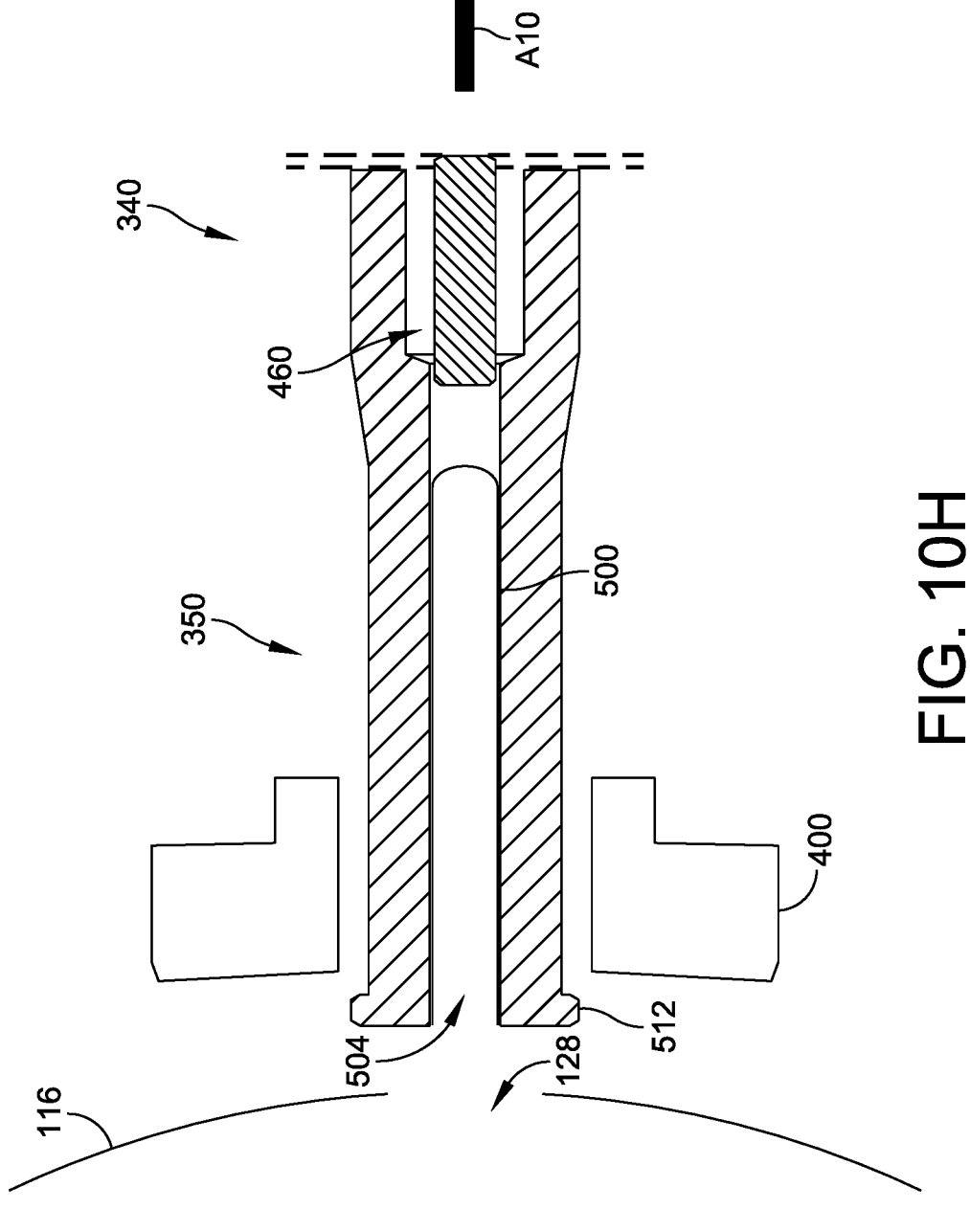
FIG. 10H shows removal of the impactor from a surgical site following impaction.

FIG. 10H shows the removal of the impactor 300 from surgical incision as indicated by an arrow A10. The surgeon can grasp the handle member 306 and withdraw the entire impactor 300 out of an incision through which the impactor 300 is placed.

After the glenosphere 116 has been impacted onto the baseplate 108 the reverse glenoid implant assembly 100 is initially assembled. If the reverse glenoid implant assembly 100 is to be completely assembled the locking screw 256 can be advanced using a driver, as illustrated in FIG. 5B. The locking screw 256 can be advanced following removal of the impactor 300 from the surgical incision.

FIG. 11 shows another handling tool in which an elongate body 340A can hold and control the glenosphere 116 and can be used separately from an impaction load applying device or structure. The elongate body 340A is similar to the inner elongate body 340 except as described differently below. The elongate body 340A includes a deflectable tip portion 350 which can be made flexible by a slot 500. The elongate body 340A can have an outer surface 550 that can be exposed in use. The elongate body 340A can be used to advance the glenosphere 116 through an incision and onto a baseplate 108. The control of the glenosphere 116 on the elongate body 340A can be similar to that described above in connection with the impactor 300. For example, the surgical wire 460 can be advanced through a control lumen 554 of the elongate body 340A to a position within the deflectable tip portion 350 to prevent deflection toward a longitudinal axis of the elongate body 340A. In other embodiments, the deflectable tip portion 350 can apply sufficient control force to the glenosphere 116 without use of a surgical wire 460. In one case, the deflectable tip portion 350 can be deflected toward the longitudinal axis of the elongate body 340A by advancing the surgical wire 460 or another control member into the control lumen 554. In another approach, an impacting device can be advanced over the outer surface 550 of the elongate body 340A, e.g., after the elongate body has been placed through the incision and the glenosphere 116 placed onto the baseplate 108. The impacting device can push the glenosphere 116 off of the deflectable tip portion 350 of the elongate body 340A, in a manner similar to that discussed above. The elongate body 340A can be combined with an impacting member to from an impactor assembly 300A along with the impacting member.

FIG. 12 shows another example of a glenoid handling tool, which can include an impactor assembly 300B that includes an elongate body 340B similar to the inner elongate body 340. The elongate body 340B can include similar structures, such as the deflectable tip portion 350. The elongate body 340B can include a control lumen extending from a proximal end to a distal end thereof. The elongate body 340B can include a threaded surface 560 disposed adjacent to a distal end thereof. The impactor assembly 300B also can include a separator 564 disposed on a distal end of the impactor assembly 300B. The separator 564 can have a threaded passage therein such that rotation of the separator 564 can be advanced by rotation of the separator 564 about the longitudinal axis of the elongate body 340B. Such rotation can cause a distal surface of the separator 564 to engage the convex articular surface of the glenosphere 116. The engagement of these surfaces can provide relative motion between the elongate body 340B and the glenosphere 116 to move a distal end of the elongate body 340B out of engagement of the glenosphere 116. The elongate body 340B can include the deflectable tip portion 350 and advancement of the separator 564 can cause the enlarged portion 512 to be deflected toward the longitudinal axis of the elongate body 340B to allow the enlarged portion 512 to be moved out of the glenosphere 116.

TERMINOLOGY

Although certain embodiments have been described herein with respect to an anatomic component or a reverse component, the implants and methods described herein can interchangeably use any articular component, including the anatomic and reverse components described herein, as the context may dictate.

As used herein, the relative terms "proximal" and "distal" shall be defined from the perspective of the implant. Thus, proximal refers to the direction of the articular component and distal refers to the direction of the base plate when the implant is assembled.

Note that the terms "first" and "second'" articular components can be used interchangeably and to refer to the anatomic components or the reverse components. Accordingly, the "first" and "second" openings can be used interchangeably and to refer to any one of the openings in the baseplate.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

The terms "approximately," "about," and "substantially" as used herein represent an amount close to the stated amount that still performs a desired function or achieves a desired result. For example, the terms "approximately," "about," and "substantially" may refer to an amount that is within less than 10% of the stated amount, as the context may dictate. As an example, in certain embodiments, the term "generally perpendicular" refers to a value, amount, or characteristic that departs from exactly perpendicular by less than about 10 degrees.

Although certain embodiments and examples have been described herein, it will be understood by those skilled in the art that many aspects of the glenoid implants shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

Any methods disclosed herein need not be performed in the order recited. The methods disclosed herein include certain actions taken by a practitioner; however, they can also include any third-party instruction of those actions, either expressly or by implication. For example, actions such as "inserting a base plate into a glenoid cavity" include "instructing insertion of a base plate into a glenoid cavity."

What is claimed is:

1. A glenosphere handling tool, comprising:
a handle assembly comprising:
    an outer elongate body extending between the proximal end and the distal end;
    an inner elongate body disposed within a first lumen defined by the outer elongate body, the inner elongate body defining a second lumen therethrough and a including a deflectable tip portion disposed at a distal end thereof; and
an actuator configured to slide the inner elongate body and deflectable tip portion relative to the outer elongate body along a longitudinal axis defined by the first lumen between a first position and a second position that is located more distal relative to the outer elongate body than the first position;
wherein, when the inner elongate body and the deflectable tip portion are disposed in the first position, the deflectable tip portion is disposed in a deflected position, and
wherein, when the inner elongate body and the deflectable tip portion are disposed in the second position, the deflectable tip portion is disposed distal of the distal end of the outer elongate body and in an undeflected position such that deflectable tip portion is sized and configured to be received within a cavity of a glenosphere and to apply a force to the glenosphere.

2. The glenoid handling tool of claim 1, wherein the actuator extends from outside the outer elongate body through a slot in the outer elongate body into engagement with a first portion of the inner elongate body.

3. The glenosphere handling tool of claim 2, wherein the first portion of the inner elongate body is enlarged compared to a second portion of the inner elongate body that is disposed distal of the first portion.

4. The glenosphere handling tool of claim 1, wherein the inner elongate body comprises an enlarged portion configured to engage a first end of a compression spring, a second end of the compression spring configured to engage an inner surface of the outer elongate body.

5. The glenosphere handling tool of claim 1, further comprising a strike plate coupled with the outer elongate body, the strike plate having an aperture aligned with the first lumen and the second lumen to provide access from the strike plate to the distal end of the inner elongate body.

6. The glenosphere handling tool of claim 1, wherein the second lumen defined by the inner elongate body is sized to slideably receive a control member in a first position in which a distal end of the control member is disposed proximal of the deflectable tip portion and a second position in which the distal end of the control member is disposed within or distal of the deflectable tip portion.

7. The glenosphere handling tool of claim 1, wherein the deflectable tip portion is configured to be maintained in the undeflected position when the lumen is occupied.

8. The glenosphere handling tool of claim 1, further comprising a compression spring, the compression spring including a first end and a second end, the first end of the compression spring configured to engage an enlarged portion of the inner elongate body, and the second end of the compression spring configured to engage an inner surface of the outer elongate body.

9. The glenosphere handling tool of claim 1, wherein the actuator is received within a slot defined by the outer elongate body that extends in a direction corresponding to a longitudinal axis of the glenosphere handling tool, the slot including a first position, a second position, and a third position.

10. The glenosphere handling tool of claim 9, wherein, when the actuator is disposed in the first position of the slot, a distal portion of the inner elongate body is fully extended from an impaction tip that is disposed at the distal end of the outer elongate body.

11. The glenosphere handling tool of claim 9, wherein the third position is disposed between the first position and the third position.

12. The glenosphere handling tool of claim 11, wherein the third position is circumferentially displaced relative to the first position and the second position.

13. The glenosphere handling tool of claim 12, wherein the deflectable tip portion is extended to engage the glenosphere when the actuator is disposed in the third position of the slot.

14. The glenosphere handling tool of claim 1, wherein the deflectable tip portion includes an enlarged portion at the distal end of the inner elongate body, the enlarged portion having a greater diameter than a diameter of a portion of the inner elongate body adjacent to the enlarged portion.

15. The glenosphere handling tool of claim 14, wherein the portion of the inner elongate body adjacent to the enlarged tip portion is located between the enlarged tip portion and a tapered portion of the inner elongate body.

16. The glenosphere handling tool of claim 15, wherein the inner elongate body defines a slot that extends from the distal end of the inner elongate body to the tapered portion of the inner elongate body.

17. A glenosphere handling tool, comprising:
an outer impactor assembly comprising an outer elongate body, a handle disposed at a proximal portion of the glenosphere handling tool, and an impaction tip at a distal portion of the glenosphere handling tool;
an inner impactor assembly comprising an inner elongate body, a deflectable distal portion, the inner elongate body slideably disposed within the outer elongate body;
a lumen disposed through the inner elongate body and the deflectable distal portion disposed at a distal end thereof; and
an actuator configured to slide the inner elongate body axially relative to the outer elongate body to move the deflectable distal portion from a first position in which the deflectable distal portion is disposed proximal of the impaction tip to a second position in which the deflectable distal portion is disposed distally of the impaction tip,
wherein the deflectable distal portion is configured to be deflected within a cavity of a glenosphere and to apply a force to the glenosphere toward the handle of the outer impactor assembly,
wherein the actuator is disposed within a slot defined by the outer elongate body, the slot defining a plurality of discrete positions along its length.

18. The glenosphere handling tool of claim 17, wherein the inner impactor assembly comprises an enlarged proximal portion and a spring member disposed between the enlarged proximal portion and an inner surface of the outer impactor assembly, the spring member configured to apply a traction force to a glenosphere toward the handle when a glenosphere is coupled with the deflectable distal portion.

19. The glenosphere handling tool of claim 17, further comprising a compression member disposed within the outer elongate body and in engagement with the inner elongate body, the compression member configured to store strain energy.

20. The glenosphere handling tool of claim 19, wherein the compression member is disposed between a proximal facing surface of the outer elongate body and a distal facing surface of the inner elongate body.

21. The glenosphere handling tool of claim 17, wherein the deflectable distal portion includes an enlarged portion disposed at a distal end of the inner elongate body.

22. The glenosphere handling tool of claim 21, wherein the inner elongate body defines a slot that extends proximally from the distal end of the inner elongate body.

23. The glenosphere handling tool of claim 17, wherein at least one position of the plurality of discrete positions along the length of the slot is circumferentially displaced relative to at least one other position of the plurality of discrete positions.

24. A glenosphere handling tool, comprising:
an elongate body comprising a proximal end and a distal end;
a retention portion disposed at the distal end of the elongate body, the retention portion comprising:
a plurality of wall segments of the elongate body separated from each other by a slot, the slot extending from a proximal end of the slot to a distal end of the slot at the distal end of the elongate body; and
an enlarged periphery at the distal end of the elongate body, the enlarged periphery comprising a proximally facing edge configured to engage an inner wall surface of a glenosphere;
wherein the retention portion is configured such that the when the retention portion is in a free state the proximally facing edge faces and may contact a surface of a glenosphere to retain the glenosphere,
wherein the retention portion is configured to be deflected at the distal end of the elongate body such that the enlarged periphery has a reduced profile for separating the handling tool from a glenosphere,
wherein the elongate body comprises an inner elongate body and further comprising an outer elongate body, the inner elongate body being slideably disposed int eh outer elongate body, and
wherein the retention portion of the inner elongate body is extended from the other elongate body of the inner elongate body and is resiliently biased toward the proximal end of the outer elongate body.

25. The glenosphere handling tool of claim 24, further comprising a control member configurable to cause the retention portion to retain a glenosphere.

26. The glenosphere handling tool of claim 25, wherein the control member has a configuration in which the control member is separated from the retention portion.

27. The glenosphere handling tool of claim 24, further comprising a wire and wherein the elongate body comprises a lumen extending between the proximal end and the distal, the retention portion being configured for retaining a glenosphere when the wire is disposed within the retention portion.

28. The glenosphere handling tool of claim 24, wherein when the inner elongate body is resiliently biased to apply a retention force on a glenosphere which retention force is transferred through the glenosphere to an impaction tip, the impaction tip applying a reaction force opposing the retention force.

29. The glenosphere handling tool of claim 24, wherein the outer elongate body comprises a slot and further comprising an actuator disposed through the slot and engaged with the inner elongate body, the actuator moveable along the slot to a first position in which the retention portion is exposed at a distal end, a second position in which the retention portion is retracted and a third position disposed between the first position and the second position.

30. The glenosphere handling tool of claim 29, wherein the slot comprises a first portion aligned with a longitudinal axis of the glenosphere handling tool and a second portion transverse to the first portion, the first position and the second position corresponding to positions along the first portion of the slot and the third position corresponding to a position along the second portion of the slot.

31. The glenosphere handling tool of claim 24, further comprising a strike plate disposed at the proximal end of the outer elongate body and an impaction tip disposed at the distal end of the outer elongate body.

32. The glenosphere handling tool of claim 31, wherein application of an impaction load causes proximal motion of the inner elongate body relative to the outer elongate body.

33. The glenosphere handling tool of claim 24, wherein the outer elongate body comprises a handle at a proximal end, an impaction tip opposite the handle, and a low profile portion disposed between the handle and the impaction tip, the low profile portion being smaller in width than both the handle portion and the impaction tip and comprising a continuously concave curve in side view.

34. The glenosphere handling tool of claim 31, wherein the impaction tip is removeably mounted to a recess in the outer elongate body.

35. The glenosphere handling tool of claim 31, wherein the impaction tip comprises an aperture configured to slideably receive the enlarged periphery of the distal end of the inner elongate body.

36. The glenosphere handling tool of claim 24, further comprising an outer member disposed over an outer surface of the elongate body, the outer member configured to be disposed on a side of a glenosphere opposite the enlarged periphery of the retention portion when the enlarged periphery has a profile configured for retaining the glenosphere.

37. The glenosphere handling tool of claim 36, wherein the outer member is configured to be moved toward the distal end of the elongate body to apply a load to a glenosphere engaged with the retention portion and to deflect the distal end of the retention portion such that the enlarged periphery has a profile to allow the retention portion to separate from the glenosphere.

* * * * *